United States Patent [19]

McFadden et al.

[11] 4,335,122
[45] Jun. 15, 1982

[54] DIHYDRO-DIBENZOXEPINES-THIEPINES AND -MORPHANTHRIDONES, COMPOSITIONS AND USE

[75] Inventors: Arthur R. McFadden, East Brunswick; Daniel E. Aultz, Middlesex, both of N.J.

[73] Assignee: Hoechst-Roussel Pharmaceuticals Inc., Somerville, N.J.

[21] Appl. No.: 225,122

[22] Filed: Mar. 18, 1981

[51] Int. Cl.³ .................. A61K 31/335; A61K 31/55; C07D 223/20; C07D 313/12
[52] U.S. Cl. .................. 424/244; 424/248.51; 424/248.53; 424/248.54; 424/248.55; 424/248.58; 424/248.4; 424/267; 424/274; 424/275; 424/278; 544/145; 544/147; 546/196; 546/202; 549/12; 549/349; 260/239.3 T; 260/330.3; 260/330.9; 548/525
[58] Field of Search ............... 544/145, 147; 260/333, 260/239.3 T, 326.34, 326.5 SA, 326.5 CA, 326.62, 330.3; 546/196, 202; 549/12; 424/244, 248.51, 248.53, 248.54, 248.55, 248.58, 248.4, 267, 274, 275, 278

[56] References Cited

U.S. PATENT DOCUMENTS

| | | | |
|---|---|---|---|
| 3,084,155 | 4/1963 | Winthrop et al. | 260/239.3 T |
| 3,420,851 | 1/1969 | Bloom et al. | 260/333 |
| 3,609,167 | 9/1971 | Zirkle | 260/333 |
| 3,639,423 | 2/1972 | Winter et al. | 260/333 |
| 4,000,288 | 12/1976 | Ackrell | 424/267 |

OTHER PUBLICATIONS

Murakami et al., *Chem. Abstracts*, vol. 80 (1974) No. P3402v.
Nipgata et al., *Chem. Abstracts*, vol. 83 (1975) No. P114,249g.

*Primary Examiner*—Robert W. Ramsuer
*Attorney, Agent, or Firm*—Jerome Rosenstock

[57] ABSTRACT

The invention relates to diuretic dihydro-dibenzoxepines-thiepines and -morphanthridones of the formula

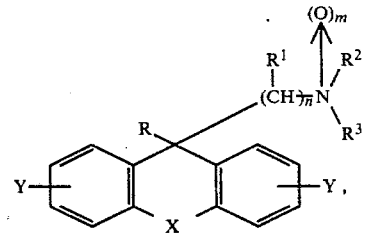

wherein R is

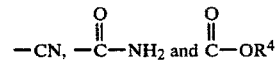

where $R^4$ is a hydrogen or an alkyl; $R^1$ is hydrogen or alkyl; $R^2$ and $R^3$ are the same or different and are hydrogen, alkyl or $R^2$ and $R^3$ are fused to form a pyrrolidino, morpholino, piperidino or azepino ring substituent; Y is hydrogen, halogen and alkoxy, X is

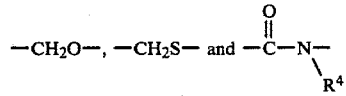

where $R^4$ is as defined above; m is an integer of 0 or 1; and n is an integer of 2 or 3; and the pharmaceutically acceptable acid addition salts thereof.

87 Claims, No Drawings

DIHYDRO-DIBENZOXEPINES-THIEPINES AND -MORPHANTHRIDONES, COMPOSITIONS AND USE

To the best of our knowledge the compounds of the present invention have not heretofore been described or suggested.

Compounds of the formula

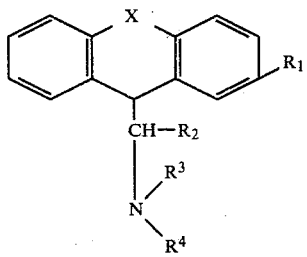

in which X is sulfur, oxymethylene, thiamethylene, thiaethylene, iminomethylene, propylene-1,3 or alkylated iminomethylene, $R_1$ is hydrogen, lower alkyl, halogen, alkoxy, trifluoromethyl or alkyl mercapto and $R_2$, $R^3$ and $R^4$ are each hydrogen or lower alkyl, described by W. Winter et al. in U.S. Pat. No. 3,639,423, are outside the scope of this invention. The same applies to the compounds of the formula

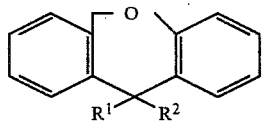

where $R^1$ is H and $R^2$ is $-O(CH_2)_2N(CH_3)_2$,

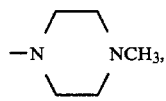

OH, and Cl or $R^1$ and $R^2$ together are $=CH-(CH_2)_2N(CH_3)_2$ or $=O$. These compounds are described by I. Jerkovsky et al., Collection Czechoslov. Chem. Commun. Vol. 32, 3448 (1967). The same applies to compounds of the formula

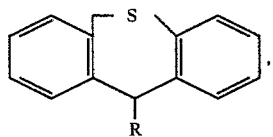

where R is H, $=O$, OH, $=NOH$, $-Cl$,

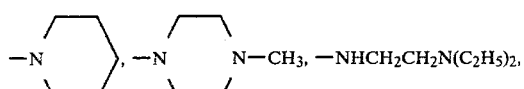

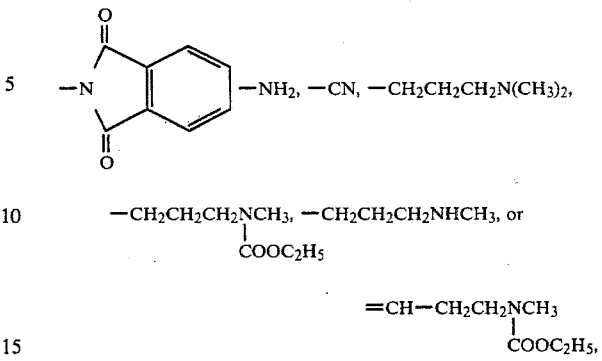

$-CH_2CH_2CH_2NCH_3$, $-CH_2CH_2CH_2NHCH_3$, or
|
$COOC_2H_5$ $=CH-CH_2CH_2NCH_3$
|
$COOC_2H_5$, as described by V. Seidlova et al., Mh. Chem. 96, 650 (1965).

The compounds of the present invention have the general formula

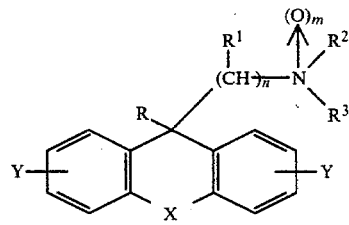

wherein R is

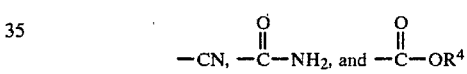

where $R^4$ is hydrogen or alkyl; $R^1$ is hydrogen or alkyl; $R^2$ and $R^3$ are the same or different and are hydrogen, alkyl, or $R^2$ and $R^3$ are fused to form a pyrrolidino, morpholino, piperidino or azepino ring substituent; Y is hydrogen, halogen and alkoxy; X is $-CH_2O-$, $-CH_2S-$ and

where $R^4$ is as defined above; m is an integer of 0 or 1; and n is an integer of 2 or 3.

In the above definitions the terms "alkyl," "alkoxy" mean the group it is describing contains from 1 to 6 carbon atoms. The term "alkyl" refers to a straight or branched chain hydrocarbon containing no unsaturation. The term "alkoxy" refers to a monovolent substituent which consists of an alkyl group linked through an ether oxygen having its free valence bond from the ether oxygen. The "halogen" refers to a member of the family consisting of fluorine, chlorine, bromine and iodine.

The compounds of the present invention are prepared in the following manner. The substituents R, $R^1$, $R^2$, $R^3$, $R^4$, X and Y and the members m and n are as defined earlier.

A toluic acid having the formula

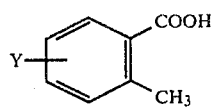

is esterified in the presence of an acid, such as H₂SO₄ by reaction with an alcohol containing 1 to 4 carbon atoms in a conventional manner, to form an alkyl ester of a toluic acid having the structural formula

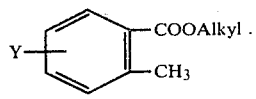

Compound II is halogenated, as for example by reaction with N-bromosuccinimide, to form an alkyl ester of an α-bromotoluic acid having the formula

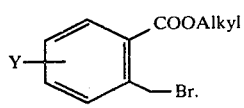

Compound III is reacted with a phenol or thiophenol of the formula

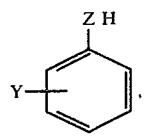

where Z is O or S to form Compound V, having the structural formula

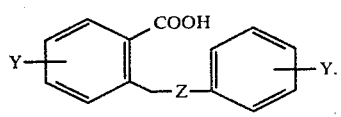

Typically, Compound III is reacted with Compound IV in the presence of an alcoholate, e.g., NaOC₂H₅, followed by hydrolysis of the ester group by treatment with a base, e.g., KOH, under conventional ester hydrolysis conditions.

Compound V is cyclized by treatment with a conventional dehydrating agent, such as polyphosphoric acid, ethanol-phosphoric pentoxide, sulfuric acid, trifluoroacetic anhydride, etc., with or without a solvent such as tetramethylene sulfone or acetic acid, to form a dibenzoxepin or a dibenzthiepin having the formula

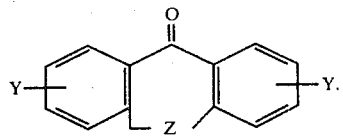

Great Britain Patent Specification No. 1,538,775 and U.S. Pat. No. 4,000,288 generally reveal adequate procedures and conditions for compounds analogous to Compound VI which procedures and conditions can be generally used to practice the synthesis of Compound VI.

The carbonyl group of the dibenzoxepin or dibenzthiepin (Compound VI) is reduced by reaction with a suitable reducing agent, e.g., NaBH₄, under conventional conditions to form Compound VII having the structural formula

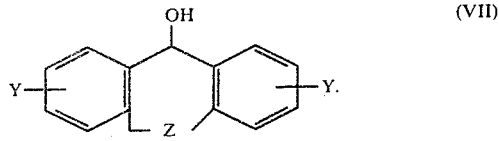

Compound VII in turn is reacted with a suitable halogenating agent, e.g., SOCl₂, to form a halogen substituted compound VIII having the formula

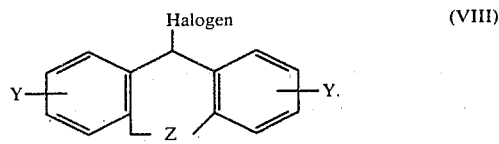

Compound VIII is converted to a cyanide by reaction with CuCN in a suitable solvent, e.g., benzene, to form Compound IX having the structural formula

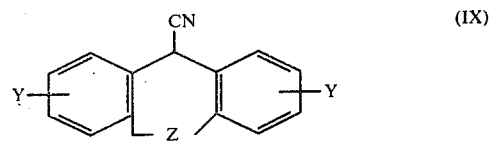

Compound IX may be subjected to solvolysis by treatment with a base, e.g., KOH, NaOH, etc., or an acid, e.g., HCl, H₂SO₄, polyphosphoric acid, etc., under conventional conditions to form a compound having the structural formula

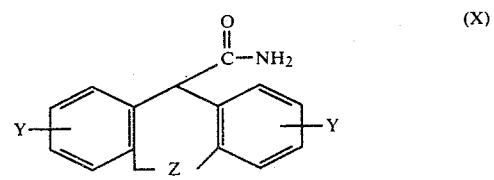

Alternatively, Compound IX may be reacted in a conventional manner with an alcohol R⁴OH in the presence of water and a suitable catalyst, e.g., hydrogen chloride, hydrogen bromide, hydrogen iodide, sulfuric acid, benzene sulfonic acid monohydrate, p-toluene sulfonic acid monohydrate, to form Compound XI having the structural formula

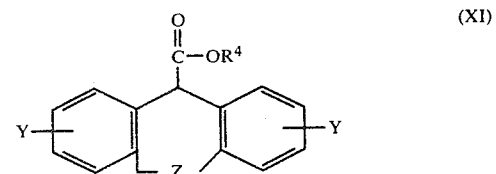

Compounds IX, X and XI are reacted with a halide having the structural formula

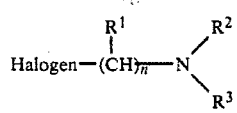

in the presence of a base such as sodium hydride to form the compounds of the invention having the general formula

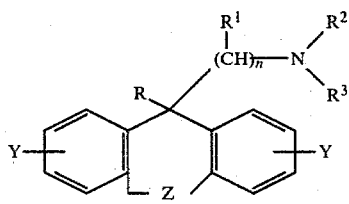

(XIII)

Typically this reaction is carried out in the presence of a suitable solvent, e.g. DMF.

To form the N-oxide, Compound XIII is typically reacted with a suitable oxidizing agent, e.g., a peracid compound such as m-chloroperbenzoic acid, to form Compound XIV of the invention having the structural formula

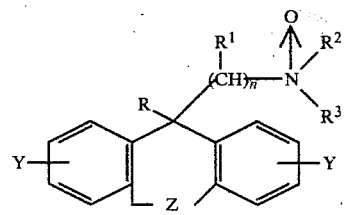

(XIV)

In an alternative procedure, Compound I can be obtained in the following manner. A substituted ortho-toluidine of the structural formula

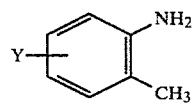

(XV)

is selected. The cyanide thereof,

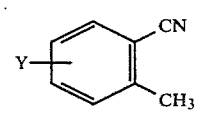

(XVI)

is prepared in a conventional manner, as by first diazotization, e.g., by reaction with a suitable cyanide such as CuCN. The cyanide group of Compound XVI is converted to carboxyl by hydrolysis in the presence of a base, e.g., KOH, to form Compound I.

Morphanthridone compounds of the invention having the structural formula

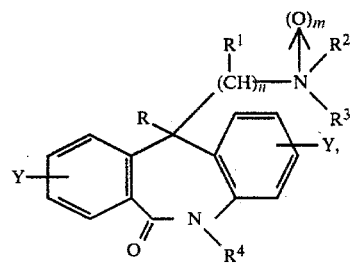

(XVII)

are prepared in the following manner.

A cyanide substituted morphanthridone having the structural formula

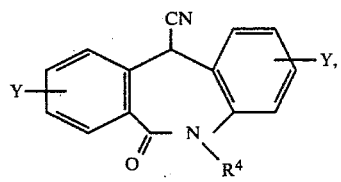

(XVIII), is prepared in a manner described by J. Ackermann, et al, Can.J.Chem. 47, 4327 (1969). Compound XVIII may be subjected to solvolysis by treatment with a base or an acid, as described above, to form Compound XIX, having the formula

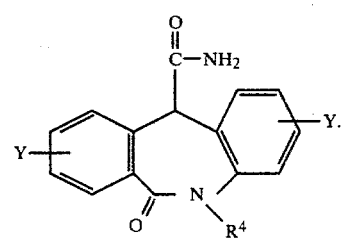

(XIX)

Alternatively Compound XVIII may be reacted in a conventional manner with an alcohol such as $R^4OH$ in the presence of water and a suitable catalyst, as described above, to form Compound XX having the structural formula

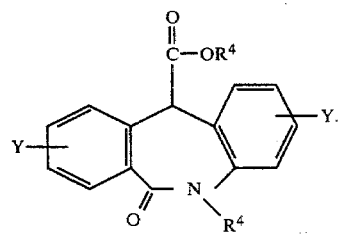

(XX)

Compounds XVIII, XIX and XX are reacted with a halide,

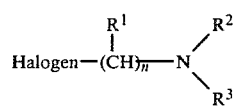

to form the compounds of the invention having the general formula

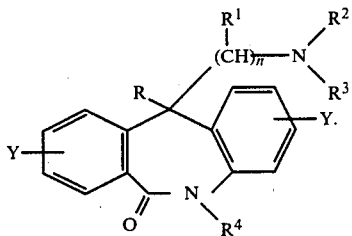

(XXI)

To form the N-oxide, Compound XXI is typically reacted with a suitable oxidizing agent, e.g., a peracid, such as m-chloroperbenzoic acid, as described above, to form a compound having the structural formula

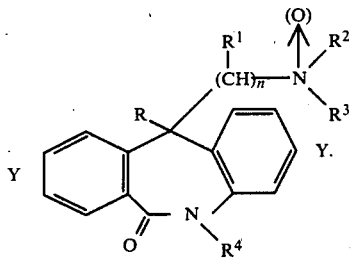

(XXII)

The compounds of the present invention are useful as diuretics. The diuretic activity of the compounds is measured in the following manner.

Groups of female Wistar rats (150-200 grams) are used and they are food deprived 16 hours prior to testing. Drugs are prepared in 1% saline and administered in a dosage volume of 15 ml/kg orally. After dosing each animal is placed in an individual metabolic cage. Water is permitted ad libitum. Urine is collected from 0-5 hours after dosing.

Each test consists of a vehicle control, a positive control group of urea treated (1000 mg/kg) and the potential diuretic agent (50 mg/kg) treated.

The individual urine samples are analyzed for sodium and/or potassium and chloride. Sodium and potassium values are typically determined using a flame photometer. Chloride determinations are typically made by a chloride analyzer. Sodium, potassium and chloride values are expressed as the mean milliequivalents (mEq)/kg/5 hrs. Diuresis is expressed as the mean milliliters (ml)/kg/5 hrs.

The mean values obtained for sodium, potassium, chloride and diuresis are expressed in a ratio to the sodium, potassium, chloride and diuresis values obtained for the urea treated group. This ratio is called the "drug to urea ratio." A drug to urea ratio greater than or equal to one for diuresis and/or sodium is indicative of diuretic activity.

The diuretic effect of some of the compounds of the invention, expressed as the ratio of (a) the mean values obtained for diuresis (urine volume) of the compound treated group to the urea treated group and (b) the mean values obtained for sodium of the compound treated group to the urea treated group, are given in Table I.

TABLE I

| COMPOUND | DOSE (ORAL) (mg/kg) | Diuresis Drug to Urea Ratio (Volume) | Sodium Drug to Urea Ratio |
|---|---|---|---|
| 11-cyano-11-[2-(dimethylamino)ethyl]-6-,11-dihydrodibenz[b,e]oxepin | 25 | 2.0 | 3.3 |
| 11-cyano-11[2-(1-piperidino)ethyl-6,11-dihydrodibenz][b,e]oxepin | 25 | 1.7 | 2.1 |
| 11-cyano-11-[2-(1-morpholino)ethyl]-6,11-dihydrodibenz[b,e]oxepin | 50 | 2.3 | 3.4 |
| 11-cyano-11-[3-(dimethylamino)-propyl]-6,11-dihydrodibenz[b,e]oxepin | 1.0 | 1.1 | 1.3 |
| 11-cyano-11-[2-(1-pyrrolidino)ethyl]-6,11-dihydrodibenz[b,e]oxepin | 5.0 | 2.1 | 3.1 |
| 11-cyano-11-[3-(1-piperidino)propyl]-6,11-dihydrodibenz[b,e]oxepin oxalate | 50 | 1.8 | 2.4 |
| 11-cyano-11-[2-(diethylamino)ethyl]-6,11-dihydrodibenz[b,e]oxepin oxalate | 50 | 2.6 | 4.2 |
| 11-cyano-11-[3-(diethylamino)propyl]-6,11-dihydrodibenz[b,e]oxepin oxalate | 50 | 1.1 | 1.2 |
| 11-cyano-11-[3-(1-pyrrolidino)propyl]-6,11-dihydrodibenz[b,e]oxepin oxalate | 50 | 1.3 | 2.0 |
| 11-cyano-11-[2-(methylamino)ethyl]-6,11-dihydrodibenz[b,e]oxepin hydrochloride | 10 | 2.0 | 1.8 |
| 11-cyano-11-[3-(dimethylamino)propyl]-6,11-dihydrodibenz[b,e]oxepin-N-oxide hydrochloride | 50 | 1.2 | 2.4 |
| 2-chloro-11-cyano-11-[3-(dimethylamino)propyl]-6,11-dihydrodibenz[b,e]oxepin hydrochloride | 50 | 1.0 | 1.4 |
| 8-chloro-11-cyano-11-[3-(dimethylamino)propyl]-6,11-dihydrodibenz[b,e]oxepin oxalate | 10 | 1.3 | 1.6 |
| 11-cyano-5,6-dihydro-5-methyl-11-[2-(dimethylamino)-ethyl]-6-morphanthridone | 50 | 2.4 | 2.5 |
| 11-cyano-5,6-dihydro-5-methyl-11-[2-(1-piperidino)ethyl]-6-morphanthridone | 25 | 2.1 | 1.8 |
| 11-cyano-5,6-dihydro-5-methyl-11[3-(dimethylamino)propyl]-6-morphanthridone | 50 | 2.2 | 3.5 |
| 11-cyano-5,6-dihydro-5-methyl-11-[3-(1-piperidino)propyl]-6- | 50 | 1.5 | 1.8 |

TABLE I-continued

| COMPOUND | DOSE (ORAL) (mg/kg) | Diuresis Drug to Urea Ratio (Volume) | Sodium Drug to Urea Ratio |
|---|---|---|---|
| morphanthridone | | | |
| 11-cyano-5,6-dihydro-5-methyl-11-[2-(diethylamino)ethyl]-6-morphanthridone | 50 | 1.2 | 1.1 |
| 11-cyano-5,6-dihydro-5-methyl-11-[3-(diethylamino)propyl]-6-morphanthridone | 10 | 1.2 | 1.8 |
| ethacrynic acid | 64 | 2.5 | |
| tienilic acid | 64 | 2.8 | |

The diuretic effect is achieved when the compounds of the invention are administered to a subject requiring such treatment at an effective oral, parenteral or intravenous dose of from 1.0 to 100 mg/kg of body weight per day. A preferred effective dose within this range is from about 10 to 50 mg/kg of body weight per day. A particularly preferred effective amount is about 10 to 25 mg/kg of body weight per day. It is to be understood, however, that for any particular subject, specific dosage regimens should be adjusted according to the individual need and the professional judgment of the person administering or supervising the administration of the compounds of the invention. It is to be further understood that the dosages set forth herein are examples only and that they do not, to any extent, limit the scope or practice of the invention.

Examples of some of the compounds of the invention are:

11-cyano-11-[2-(butylethylamino)ethyl]-6,11-dihydrodibenz[b,e]oxepin;
11-[2-(butylpentylamino propyl]-11-cyano-6,11-dihydrodibenz[b,e]oxepin;
11-carboxy-3-chloro-11-[2-(diethylamino)ethyl]-6,11-dihydrodibenz[b,e]oxepin;
11-cyano-4-ethoxy-11-[3-(ethylmethylamino)propyl]-6,11-dihydrodibenz[b,e]oxepin;
11-cyano-11-[2-(amino)ethyl]-6,11-dihydrodibenz[b,e]oxepin;
11-cyano-11-[2-(dibutylamino)ethyl]-6,11-dihydrodibenz[b,e]oxepin-N-oxide;
9-bromo-11-cyano-11-[3-(ethylpropylamino)propyl]-6,11-dihydrodibenz[b,e]oxepin-N-oxide;
7-butoxy-11-cyano-11-[3-(ethylpentylamino)propyl]-6,11-dihydrodibenz[b,e]oxepin-N-oxide;
9-chloro-11-cyano-11-[3-aminopropyl]-6,11-dihydrodibenz[b,e]oxepin-N-oxide;
3-bromo-11-cyano-11-[2-(1-piperidino)ethyl]-6,11-dihydrodibenz[b,e]oxepin;
11-cyano-4-ethoxy-11-[3-(1-piperidino)propyl]-6,11-dihydrodibenz[b,e]oxepin;
8-chloro-11-ethoxycarbonyl-11-[3-(1-morpholino)propyl]-6,11-dihydrodibenz[b,e]oxepin;
11-cyano-5-pentoxy-11-[2-(1-morpholino)ethyl]-6,11-dihydrodibenz[b,e]oxepin;
9-bromo-11-cyano-[3-(hexamethyleneimino)propyl]-6,11-dihydrodibenz[b,e]oxepin;
2-methoxy-11-cyano-11-[2-(1-pyrrolidino)ethyl]-6,11-dihydrodibenz[b,e]oxepin;
11-carbamoyl-11-[2-(butylpentylamino)ethyl]-6,11-dihydrodibenz[b,e]oxepin;
11-carbamoyl-4-chloro-11-[2-(diethylamino)ethyl]-6,11-dihydrodibenz[b,e]oxepin;
4-butoxy-11-carbamoyl-11-[3-(ethylmethylamino)propyl]-6,11-dihydrodibenz[b,e]oxepin;
11-methoxycarboxyl-11-[2-aminoethyl]-6,11-dihydrodibenz[b,e]oxepin;
11-carbamoyl-11-[2-(diethylamino)ethyl]-6,11-dihydrodibenz[b,e]oxepin-N-oxide;
9-chloro-11-carboxy-11-[3-(methylpropylamino)propyl]-6,11-dihydrodibenz[b,e]oxepin-N-oxide;
7-butoxy-11-carbamoyl-11-[3-(dimethylamino)propyl]-6,11-dihydrodibenz[b,e]oxepin-N-oxide;
3-bromo-11-carbamoyl-11-[2-(1-piperidino)ethyl]-6,11-dihydrodibenz[b,e]oxepin;
11-carbamoyl-4-ethoxy-11-[3-(1-piperidino)propyl]-6,11-dihydrodibenz[b,e]oxepin;
11-carbamoyl-5-chloro-11-[3-(1-morpholino)propyl]-6,11-dihydrodibenz[b,e]oxepin;
11-carbamoyl-6-pentoxy-11-[2-(1-morpholino)ethyl]-6,11-dihydrodibenz[b,e]oxepin;
8-bromo-11-carbamoyl-11-[3-(hexamethyleneimino)propyl]-6,11-dihydrodibenz[b,e]oxepin;
11-carboxy-11-[3-(dimethylamino)propyl]-6,11-dihydrodibenz[b,e]oxepin;
11-carbamoyl-2-methoxy-11-[2-(1-pyrrolidino)ethyl]-6,11-dihydrodibenz[b,e]oxepin;
11-cyano-5,6-dihydro-5-methyl-11-(2-aminoethyl)-6-morphanthridone;
11-cyano-5,6-dihydro-11-(2-aminoethyl)-6-morphanthridone;
11-cyano-3-hexyl-5,6-dihydro-11-[3-(diethylamino)propyl]-6-morphanthridone;
4-bromo-11-cyano-5-propyl-5,6-dihydro-11-[2-(ethylmethylamino)ethyl]-6-morphanthridone;
11-cyano-8-ethoxy-5-methyl-5,6,-dihydro-11-[2-(dimethylamino)ethyl]-6-morphanthridone;
11-cyano-5-methyl-5,6,-dihydro-11-[3-(diethylamino)propyl]-6-morphanthridone-N-oxide;
9-bromo-11-cyano-5-propyl-5,6-dihydro-11[3-(butylpropylamino)propyl]-6-morphanthridone-N-oxide;
7-butoxy-11-cyano-5-methyl-5,6-dihydro-11-[2-(diethylamino)ethyl]-6-morphanthridone-N-oxide;
9-chloro-5-ethyl-11-cyano-11-[2-(dipropylamino)ethyl]-5,6-dihydro-6-morphanthridone-N-oxide;
3-bromo-11-cyano-5-methyl-11-[2-(1-pyrrolidino)ethyl]-6-morphanthridone;
11-cyano-4-ethoxy-5-methyl-5,6-dihydro-11-[3-(1-piperidino)propyl]-6-morphanthridone;
8-chloro-11-cyano-5,6-dihydro-5-ethyl-11-[3-(1-morpholino)propyl]-6-morphanthridone;
11-cyano-5,6-dihydro-5-methyl-7-pentoxy-11-[2-(1-morpholino)ethyl]-6-morphanthridone;
9-bromo-5-butyl-11-cyano-11-[3-(hexamethyleneimino)propyl]-5,6-dihydro-6-morphanthridone;
11-cyano-5,6-dihydro-2-methoxy-5-pentyl-11-[2-(1-pyrrolidino)ethyl]-6-morphanthridone;
11-carbamoyl-5-methyl-11-[2-(dimethylamino)ethyl]-5,6-morphanthridone;
11-carbamoyl-5,6-dihydro-11-(2-aminoethyl)-6-morphanthridone;
11-carbamoyl-3-hexyl-11-[3-(diethyl-amino)propyl]-5,6-dihydro-6-morphanthridone;

4-bromo-11-carbamoyl-5,6-dihydro-5-propyl-11-[2-(ethylmethylamino)ethyl]-6-morphanthridone;
11-carbamoyl-5,6-dihydro-8-ethoxy-5-methyl-11-[2-(dimethylamino)ethyl]-6-morphanthridone;
11-carbamoyl-5,6-dihydro-5-methyl-11-[3-(diethylamino)propyl]-6-morphanthridone-N-oxide;
9-bromo-11-carbamoyl-5,6-dihydro-5-propyl-11-[3-(butylpropylamino)propyl]-6-morphanthridone-N-oxide;
7-butoxy-11-carbamoyl-5,6-dihydro-5-methyl-11-[(2-diethylamino)ethyl]-6-morphanthridone;
11-carbamoyl-9-chloro-5,6-dihydro-5-ethyl-11-[2-(dipropylamino)ethyl]-6-morphanthridone-N-oxide;
3-bromo-11-carbamoyl-5,6-dihydro-5-methyl-11-[2-(1-pyrrolidino)ethyl]-6-morphanthridone;
11-carbamoyl-5,6-dihydro-4-ethoxy-5-methyl-11-[3-(1-piperidino)propyl]-5,6-dihydro-6-morphanthridone;
11-carbamoyl-8-chloro-5,6-dihydro-5-ethyl-11-[3-(1-morpholino)propyl]-6-morphanthridone;
11-carbamoyl-5,6-dihydro-5-methyl-7-pentoxy-11-[2-(1-morpholino)ethyl]-6-morphanthridone;
9-bromo-5-butyl-11-carbamoyl-5,6-dihydro-11-[3-(azepino)propyl]-6-morphanthridone;
11-carbamoyl-5,6-dihydro-2-methoxy-5-pentyl-11-[2-(1-pyrrolidino)ethyl]-6-morphanthridone;
11-cyano-11-(2-aminoethyl)-6,11-dihydrodibenz[b,e]thiepin;
11-cyano-11-[2-(butylpropylamino)-ethyl]-6,11-dihydrodibenz[b,e]thiepin;
11-cyano-11-[2-(butylpentylamino)ethyl]-6,11-dihydrodibenz[b,e]thiepin;
3-chloro-11-cyano-11-[2-(diethylamino)ethyl]-6,11-dihydrodibenz[b,e]thiepin;
11-cyano-4-ethoxy-11-[3-(ethylmethylamino)propyl]-6,11-dihydrodibenz[b,e]thiepin;
11-cyano-11-[2-(dibutylamino)ethyl]-6,11-dihydrodibenz[b,e]thiepin-N-oxide;
9-bromo-11-cyano-11-[3-(ethylpropylamino)propyl]-6,11-dihydrodibenz[b,e]thiepin-N-oxide;
7-butoxy-11-cyano-11-[3-(ethylphenylamino)propyl]-6,11-dihydrodibenz[b,e]thiepin-N-oxide;
9-chloro-11-cyano-11-(3-aminopropyl)-6,11-dihydrodibenz[b,e]thiepin-N-oxide;
3-bromo-11-cyano-11-[2-(1-piperidino)ethyl]-6,11-dihydrodibenz[b,e]thiepin;
11-cyano-4-ethoxy-11-[3-(1-piperidino)-propyl]-6,11-dihydrodibenz[b,e]thiepin;
8-chloro-11-cyano-11-[3-(1-morpholino)-propyl]-6,11-dihydrodibenz[b,e]thiepin;
11-cyano-5-pentoxy-11-[2-(1-morpholino)-ethyl]-6,11-dihydrodibenz[b,e]thiepin;
9-bromo-11-cyano-11-[3-(azepino)propyl]-6,11-dihydrodibenz[b,e]thiepin;
11-cyano-2-methoxy-11-[2-(1-pyrrolidino)-ethyl]-6,11-dihydrodibenz[b,e]thiepin;
11-carbamoyl-11-[2-(butylpentylamino)ethyl]-6,11-dihydrodibenz[b,e]thiepin;
11-carbamoyl-4-chloro-11-[2-(diethylamino)ethyl]-6,11-dihydrodibenz[b,e]thiepin;
4-butoxy-11-carbamoyl-11-[3-(ethylmethylamino)-propyl]-6,11-dihydrodibenz[b,e]thiepin;
11-carbamoyl-11-[2-aminoethyl]-6,11-dihydrodibenz[b,e]thiepin;
11-carbamoyl-11-[2-(diethylamino)ethyl]-6,11-dihydrodibenz[b,e]thiepin-N-oxide;
11-carbamoyl-9-chloro-11-[3-(methylpropylamino)-propyl]-6,11-dihydrodibenz[b,e]thiepin-N-oxide;
7-butoxy-11-carbamoyl-11-[-3-(dimethylamino)propyl]-6,11-dihydrodibenz[b,e]thiepin-N-oxide;
3-bromo-11-carbamoyl-11-[2-(1-piperidino)ethyl]-6,11-dihydrodibenz[b,e]thiepin;
11-carbamoyl-4-ethoxy-11-[3-(1-piperidino)propyl]-6,11-dihydrodibenz[b,e]thiepin;
11-carbamoyl-5-chloro-11-[3-(1-morpholino)propyl]-6,11-dihydrodibenz[b,e]thiepin;
11-carbamoyl-6-pentoxy-11-[2-(1-morpholino)ethyl]-6,11-dihydrodibenz[b,e]thiepin;
8-bromo-11-carbamoyl-11-[3-(hexamethyleneimino)-propyl]-6,11-dihydrodibenz[b,e]thiepin;
11-carbamoyl-2-methoxy-11-[2-(1-pyrrolidino)ethyl]-6,11-dihydrodibenz[b,e]thiepin.

Effective amounts of the compounds of the present invention may be administered to a subject by one of various methods, for example, orally as in capsules or tablets, parenterally in the form of sterile solutions or suspensions, and in some cases intravenously in the form of sterile solutions. The compounds of the invention, while effective themselves, may be formulated and administered in the form of their pharmaceutically acceptable acid addition salts for purposes of stability, convenience of crystallization, increased solubility and the like.

Preferred pharmaceutically acceptable acid addition salts include those derived from inorganic acids such as hydrochloric, hydrobromic, sulfuric, nitric, phosphoric, perchloric acids and the like as well as organic acids such as tartaric, citric, acetic, succinic, maleic, fumaric acids and the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of at least one compound of the invention, the active ingredient, but may be varied depending upon the particular form and may conveniently be between 4% to about 70% of the weight of the unit. The amount of the compound present in such compositions is such that a suitable dosage will be obtained. Preferred compositions and preparations according to the present invention are prepared so that an oral dosage unit form contains between 5.0–300 milligrams of the particular compound of the invention.

The tablets, pills, capsules, troches and the like may also contain the following adjuvants: a binder such as microcrystalline cellulose, gum tragacanth or gelatin; an excipient such as starch or lactose; a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of the compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the following adjuvants: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The following examples are for illustrative purposes and are not to be construed as limiting the invention disclosed herein. All temperatures are given in degrees centigrade.

In view of the amendments to the Manual of Patent Examining Procedure, including Sections 608.01(p); 707.07(l); 2004; 2012 dated January, 1981 and received on or about the week of Sept. 14, 1981, the Example of the specification is to be read as if it were expressed in the past tense since it is an example which has actually been carried out.

EXAMPLE 1

A. 11-Cyano-6,11-dihydrodibenz[b,e]oxepin

11-Chloro-6,11-dihydrodibenz[b,e]oxepin (32.69 g; 0.14 mole) is dissolved in dry benzene (300 ml) and placed under a dry nitrogen atmosphere. To this solution is added in one portion, CuCN (32.04 g; 0.35 mole). The reaction is heated to reflux for 3½ hours and filtered while hot. After washing the salts with benzene, the filtrate is removed in vacuo to give a solid. This solid is triturated several times with isopropyl ether and finally hexane to give a solid (92%) of 11-cyano-6,11-dihydrodibenz[b,e]oxepin m.p. 65°–66.5° C.

B. 11-Cyano-11-[2-(Dimethylamino)ethyl]-6,11-dihydrodibenz[b,e]oxepin

Sodium hydride (5.0 g; 0.10 mole) is added portionwise with cooling (5°–10° C.) under a nitrogen atmosphere to a solution of 11-cyano-6,11-dihydrodibenz[b,e]oxepin of Example 1A, (20.0 g; 0.09 mole) in dry DMF (200 ml). After thirty minutes, effervescence ceases and 2-dimethylaminoethyl chloride (10.0 g; 0.09 mole) in dimethyl formamide [DMF] (200 ml) is added dropwise. Stirring is continued at 80° C. for sixteen hours. The reaction is cooled and poured into three liters of water. After extraction with ether, the ether is re-extracted with 1 N HCl, and the combined aqueous extracts are made basic with 50% NaOH. After extracting with ether and drying ($K_2CO_3$), the solvent is removed in vacuo to provide an oil which is chromatographed on an alumina column. The resulting oil crystallizes upon standing and trituration with hexane yields 11.0 g (42%) of a solid of 11-cyano-11-[2-(dimethylamino)ethyl]-6,11-dihydrodibenz[b,e]oxepin (m.p. 63°–65° C.), ANALYSIS: Calculated for $C_{19}H_{20}N_2O$: 78.04%C; 6.89%H; 9.58%N. Found: 78.05%C; 7.11%H; 9.55%N.

EXAMPLE 2

11-cyano-11-[2-(1-piperidino)ethyl]-6,11-dihydrodibenz[b,e]oxepin

To a solution of 11-cyano-6,11-dihydrodibenz[b,e]oxepin (21.38 g, 0.096 mole) of Example 1A, in dry DMF (200 ml) under nitrogen is added sodium hydride (5.75 g, 0.24 mole) portionwise while keeping the temperature below 5° C. Upon completion of the addition, the reaction is allowed to come to ambient temperature and stirring is continued for one hour. At this time a suspension of N-(2-chloroethyl)piperidine hydrochloride (26.5 g, 0.14 mole) in dimethylformamide (DMF) (200 ml) is added while maintaining the temperature below 10° C. The reaction is then stirred at 70°–80° C. for 18 hours, cooled and poured into 2,500 ml of ice water. The resulting solid is extracted with ether; the ether back extracted with 2 N HCl and the acidic washes combinded and made basic with potassium carbonate. The resulting solid is filtered, washed with water and dried. The resultant solid is chromatographed on alumina to give 10.0 g (32%) of a solid of 11-cyano-11-[2-(1-piperidino)ethyl]-6,11-dihydrodibenz[b,e]oxepin (m.p. 70°–72° C.).

ANALYSIS: Calculated for $C_{22}H_{24}N_2O$: 79.48%C; 7.27%H; 8.42%N. Found: 79.18%C; 7.30%H; 8.25%N.

EXAMPLE 3

11-Cyano-11-[2-(1-Morpholino)ethyl]-6,11-dihydrodibenz[b,e]oxepin

Sodium hydride (4.28 g; 0.18 mole) is added portionwise with cooling (5°–10° C.) under a nitrogen atmosphere to a solution of 11-cyano-6,11-dihydrodibenz[b,e]-oxepin of Example 1A (16.0 g; 0.072 mole) in dry DMF (320 ml). Upon completion of the addition, the reaction mixture is stirred at ambient temperature for one hour and cooled to 5° C. At this time N-(2-chloroethyl)-morpholine hydrochloride (18.75 g; 0.10 mole) is added portion wise at a rate to maintain the temperature below 10° C. The reaction is heated at 70°–80° C. for 20 hours, cooled and poured into 2 liters of ice water. After extraction with ether, the ether is back extracted with 2 N HCl and the combined acidic extracts are made basic with potassium carbonate. After extraction with ether and drying ($K_2CO_3$), the solvent is removed in vacuo to provide a solid which is chromatographed on alumina. The resulting solid is triturated with hexane (three-fifty ml. portions) and dried to give 10.0 g (42%) of a solid of 11-cyano-11-[2-(1-morpholino)ethyl]-6,11-dihydrodibenz[b,e]oxepin (m.p. 101°–103° C.).

ANALYSIS: Calculated for $C_{21}H_{22}N_2O_2$: 75.42%C; 6.63%H; 8.37%N. Found: 75.58%C; 6.77%H; 8.55%N.

EXAMPLE 4

11-cyano-11-[3-(dimethylamino)propyl]-6,11-dihydrodibenz[b,e]oxepin

Sodium hydride (4.28 g; 0.18 mole) is added portionwise with cooling (5°–10° C.) under nitrogen to a solution of 11-cyano-6,11-dihydrodibenz[b,e]oxepin (16.0 g; 0.72 mole), of Example 1A, in dry DMF (320 ml) and stirred at ambient temperature for 1½ hours. At this time, 2-dimethylaminopropyl chloride hydrochloride (15.92 g; 0.10 mole) is added portionwise while maintaining the temperature below 10° C. Upon completion of the addition, stirring is continued at 80° C. for 20 hours. The reaction mixture is cooled, poured into 2 liters of ice water and extracted with ether. The ether is back extracted with 2 N HCl and the acidic washes combined and made basic with potassium carbonate. After extraction with ether and drying ($K_2CO_3$) the ether is removed in vacuo to give a solid. Trituration with hexane and drying provides 7.0 g (32%) of a solid (m.p. 112°–114° C.) of 11-cyano-11-[3-(dimethylamino)propyl]-6,11-dihydrodibenz[b,e]oxepin.

ANALYSIS: Calculated for $C_{20}H_{22}N_2O$: 78.39%C; 7.23%; 9.13%N. Found: 78.11%C; 7.24%H; 9.33%N.

EXAMPLE 5

11-Cyano-11-[3-(dimethylamino)propyl]-6,11-dihydrodibenz[b,e]oxepin hydrochloride A solution of 11-cyano-11-[3-(dimethylamino)propyl]-6,11-dihydrodibenz[b,e]oxepin of Example 4 (3.0 g; 0.009 mole) in dry ether is vigorously stirred and cooled in an ice bath. A saturated solution of HCl in ether is added dropwise until no more salt precipitates. The salt is filtered, washed with ether and dried. Two recrystallizations from methanol-ether provide 1.1 g of crystals of 11-cyano-11-[3-dimethylamino)propyl[-6,11-dihydrodibenz[b,e]oxepin hydrochloride, m.p. 219° C.

ANALYSIS: Calculated for $C_{20}H_{23}ClN_2O$: 70.06%C; 6.76%H; 8.17%N; 10.34%Cl. Found: 70.18%C; 6.93%H; 8.06%N; 10.38%Cl.

EXAMPLE 6

11-Cyano-11-[3-(methylamino)propyl]-6,11-dihydrodibenz[b,e]oxepin hydrochloride

A mixture of 2.90 g (0.0095 mole) of 11-cyano-11-[3-(dimethylamino)propyl]-6,11-dihydrodibenz[b,e]oxepin of Example 4, 6.0 g (0.028 mole) of 2,2,2-trichloroethyl chloroformate and 50 ml of dry benzene is refluxed for 17 hours, cooled and 50 ml of ether added. The solution is washed with 2 N HCl, water, dried ($CaSO_4$), filtered and concentrated in vacuo to an oil. The oil is dissolved in 15 ml of acetic acid and 4.3 g (0.066 mole) of zinc dust is added with stirring. After the reaction becomes exothermic, the suspension is cooled and stirred at ambient temperature for 3 hours. After filtering off the precipitate, the filtrate is basified with 10% sodium hydroxide and extracted with ether. Drying ($K_2CO_3$), filtering and concentrating in vacuo provides an oil which is dissolved in dry ether and treated with dry HCl gas to yield a hydrochloride which is dissolved in dry ethanol and concentrated to a semi-solid. Triturating of the solid with methanol-ether yields a solid which is recrystallized from acetonitrile to provide crystals of 11-cyano-11-[3-(methylamino)propyl]-6,11-dihydrodibenz[b,e]oxepin hydrochloride, m.p. 137°–139° C.

ANALYSIS: Calculated for $C_{19}H_{21}ClN_2O$: 69.39%C; 6.44%H; 8.52%N. Found: 69.11%C; 6.48%H; 8.65%N.

EXAMPLE 7

11-Carbamoyl-11-[3-dimethylamino)propyl]-6,11-dihydrodibenz[b,e,[oxepin hydrochloride To a solution of 11-[3-(dimethylamino)propyl]-11-cyano6,11-dihydrodibenz[b,e]oxepin of Example 4 (4.0 g; 0.013 mole) in 2-ethoxyethanol (25 g) is added 15% aqueous KOH (11 g) and the solution refluxed for twenty hours. The reaction is cooled, filtered and the solvent removed in vacuo. Water is added to the residue and the gum that forms slowly solidifies. The solid is filtered and the filtrate extracted with $CHCl_3$. After drying ($K_2CO_3$) and concentration in vacuo the resultant oil is dissolved in ether and treated with etheral HCl. The solid is filtered, washed with ether and dried to yield 1.95 g (75% yield) of 11-carbamoyl-11-[3-(dimethylamino)propyl]-6,11-dihydrodibenz[b,e]oxepin hydrochloride, m.p. 145° C. (decomposition).

ANALYSIS: Calculated for $C_{20}H_{25}ClN_2O_2$: 66.57%C; 6.98%H; 7.76%N. Found: 66.03%C; 7.24%H; 7.80%N.

EXAMPLE 8

11-Cyano-11-[3-(Dimethylamino)propyl]-6,11-dihydrodibenz[b,e]oxepin-N-oxide hydrochloride To 2.00 g (0.007 mole) of 11-[3-(dimethylamino)propyl]-11-cyano-6,11-dihydrodibenz[b,e]oxepin of Example 4 in 30 ml of dry dichloromethane is added at 10° C. 1.50 g (0.009 mole) of 85% m-chloroperbenzoic acid and the solution is stirred at ambient temperature for 4 hours. The solvent is concentrated in vacuo and the oil chromatographed on a silica gel column with 20% methanol-benzene and then pure methanol. Concentration in vacuo of the combined methanol fractions provides an oil which is dissolved in dry ether (a little methanol added) and treated with HCl gas to form a precipitate. Recrystallization from methanol-ether (1:2) followed by a second recrystallization from acetonitrile yields 0.5 g (25%) of crystals of 11-cyano-11-[3-(dimethylamino)propyl]-6,11-dihydrodibenz[b,e]oxepin-N-oxide hydrochloride, m.p. 167°–169° C.

A yield of 70% is obtained if tetrahydrofuran (THF) is used as solvent and the hydrochloride is formed in situ by addition of ethanolic hydrochloride followed by dilution with ether at 0°–2° C.

ANALYSIS: Calculated for $C_{21}H_{22}ClN_2O_2$: 66.93%C; 6.46%H; 7.81%N. Found: 66.50%C; 6.52%H; 7.88%N.

EXAMPLE 9

11-Cyano-11-[2-(1-pyrrolidino)ethyl]-6,11-dihydrodibenz[b,e]oxepin

11-Cyano-6,11-dihydrodibenz[b,e]oxepin (16.0 g, 0.072 mole) of Example 1A is dissolved in dry DMF (300 ml) and to this is added sodium hydride (4.31 g, 0.18 mole) portionwise while maintaining the temperature below 5° C. Upon completion of the addition, the reaction is allowed to come to ambient temperature and stirring continued for 1.5 hours. The solution is cooled to 5° C. and N-(2-chloroethyl) pyrrolidine hydrochloride (18.36 g, 0.108 mole) is added portionwise while maintaining the temperature below 10° C. Stirring is continued at ambient temperature for 18 hours. The reaction mixture is poured with stirring into two liters of ice water and extracted with ether. The ether is back extracted with 2 N HCl and the acidic extracts combined and made basic with 10% NaOH. The resulting precipitate is filtered, dried and recrystallized from isopropanol to provide 5.63 g (25%) of a solid 11-cyano-11-[2-(1-pyrrolidino)ethyl]-6,11-dihydrodibenz[b,e]oxepin, m.p. 93°–95° C.

ANALYSIS: Calculated for $C_{21}H_{22}N_2O$: 79.21%C; 6.96%H; 8.70%N. Found: 78.77%C; 7.05%H; 8.56%N.

EXAMPLE 10

11-Cyano-11-[3-(1-piperidino)propyl]-6,11-dihydrodibenz[b,e]oxepin oxalate

To a solution of 11-cyano-6,11-dihydrodibenz[b,e]oxepin of Example 1A (15.0 g, 0.067 mole) in dry DMF (300 ml) is added NaH (1.76 g; 0.073 mole) portionwise while maintaining the temperature below 5° C. Upon completion of the addition, the reaction is allowed to come to ambient temperature and stirring continued for one hour. The reaction is cooled to 10° C. and N-(3-chloropropyl)-piperidine (11.93 g; 0.073 mole) in DMF is added dropwise and stirring continued at ambient temperature for 20 hours. After pouring into 2 liters of ice water and extraction with ether, the ether is back extracted with 2 N HCl. The acidic extracts are combined and made basic with sodium hydroxide. After extraction with ether and drying ($K_2CO_3$), removal of the solvent in vacuo gives an oil which is chromatographed on alumina to yield 2.5 g, (11%) of product. 11-Cyano-11-[3-(1-piperidino)propyl]-6,11-dihydrodibenz[b,e]oxepin oxalate, m.p. 178°–180° C. is prepared by addition of oxalic acid and recrystallization from methanol/ether.

ANALYSIS: Calculated for ($C_{23}H_{26}N_2O$: 68.79%C; 6.46%H; 6.41%N. Found: 68.44%c; 6.47%H; 6.34%N.

EXAMPLE 11

11-Cyano-11-[2-(diethylamino)ethyl]-6,11-dihydrodibenz[b,e]oxepin oxalate

To a solution of 11-cyano-6,11-dihydrodibenz[b,e]oxepin (9.6 g; 0.043 mole) of Example 1A, in dry DMF (150 ml) is added sodium hydride (1.13 g; 0.047 mole) portionwise at 5° C. under a nitrogen atmosphere. Upon completion of the addition, the reaction is allowed to come to ambient temperature and stirring is continued for 1½ hours. At this time 2-diethylaminoethyl chloride (6.37 g; 0.047 mole) in DMF is added dropwise and stirring continued for 20 hours. The reaction is poured into two liters of ice water and extracted with ether. The ether is back extracted with 2 N HCl and the acidic extracts combined and made basic with NaOH. After extraction with ether and drying ($K_2CO_3$), removal of the solvent in vacuo provides an oil. The oil is chromatographed on alumina to give 4.2 g (305) of an oil. An oxalate of 11-cyano-11-[2-(diethylamino)ethyl]-6,11-dihydrodibenz[b,e]oxepin m.p. 87°–90° C. (turbid) is prepared by addition of oxalic acid and recrystallized from ethyl acetate.

ANALYSIS: Calculated for $C_{23}H_{26}N_2O_5$: 67.29%C; 6.38%H; 6.82%N. Found: 66.83%C; 6.56%H; 6.63%N.

EXAMPLE 12

11-Cyano-11-[2(hexamethyleneimino)ethyl]-6,11-dihydrodibenz[b,e]oxepin oxalate

To a solution of 11-cyano-6,11-dihydrodibenz[b,e]oxepin of Example 1A (7.2 g; 0.032 mole) in dry DMF (110 ml) at 5° C. is added sodium hydride (1.9 g; 0.08 mole) portionwise under a nitrogen atmosphere. After stirring at ambient temperature for 1½ hours, the reaction is cooled to 10° C. and 2-(hexamethyleneimino)ethyl chloride hydrochloride (6.9 g; 0.035 mole) is added portionwise. Stirring is continued at 100° C. for 2½ hours. The reaction is cooled and poured into two liters of ice water, extracted with ether and the ether back extracted with 2 N HCl. The acidic extracts are combined and made basic with sodium hydroxide. After extracting with ether, washing with a saturated NaCl solution and drying ($K_2CO_3$), the ether is removed in vacuo to provide 3.0 g of an oil (27%). An oxalate of 11-cyano-11-[2-(hexamethylene imino)ethyl]-6,11-dihydrodibenz[b,e]oxepin, m.p. 195°–197° C., is prepared by addition of oxalic acid and recrystallization from ethanol.

ANALYSIS: Calculated for $C_{25}H_{28}N_2O_5$: 68.78%C; 6.46%H; 6.41%N. Found: 69.16%C; 6.59%H; 6.29%N.

EXAMPLE 13

11-Cyano-11-[3-(diethylamino)propyl]-6,11-dihydrodibenz[b,e]oxepin oxalate

To a solution of 11-cyano-6,11-dihydrodibenz[b,e]oxepin of Example 1A (15.0 g; 0.067 mole) in dry DMF (300 ml) is added sodium hydride (4.01 g; 0.167 mole) portionwise at 5° C. under a nitrogen atmosphere. Upon completion of the addition, the reaction is stirred at ambient temperature for one hour. At this time, diethylaminopropyl chloride (13.71 g; 0.073 mole) is added portionwise at 10° C. and stirring continued at ambient temperature for 18 hours. The reaction mixture is poured into 2 liters of ice water and extracted with ether. The ether is back extracted with 2 N HCl and the combined acidic extracts made basic with sodium hydroxide. After extraction with ether and drying ($K_2CO_3$), removal of the solvent in vacuo provides an oil which is chromatographed on alumina (2.5 g; 11%). An oxalate of 11-cyano-11-[3-(diethylamino)propyl]-6,11-dihydrodibenz[b,e]oxepin, m.p. 113°–116° C. is prepared by addition of oxalic acid and recrystallized from acetone.

ANALYSIS: Calculated for $C_{24}H_{28}N_2O_5$: 67.90%C; 6.64%H; 6.60%N. Found: 67.70%; 6.65%H; 6.44%N.

EXAMPLE 14

11-Cyano-11-[3-(1-pyrrolidino)propyl]-6,11-dihydrodibenz[b,e]oxepin oxalate

To 4.00 g (0.18 mole) of 11-cyano-6,11-dihydrodibenz[b,e]oxepin of Example 1A in 70 ml of dry DMF is added at 4° C. in two portions 0.50 g (0.20 mole) of 99% sodium hydride. After vigorous evolution has ceased, the ice bath is removed and the mixture stirred at ambient temperature for one hour. The solution is cooled to 5° C. and 3.00 g (0.20 mole) of pyrrolidinopropyl chloride in 20 ml of dry DMF is added dropwise and the solution heated at 63° C. for three hours. After decanting into 1.5 liters of ice water, the product is extracted with ether and the ether then extracted with 2 N.HCl. Basification of the acid solution followed by extraction with ether, drying ($K_2CO_3$), filtering, and concentration in vacuo provides a solid which is dissolved in anhydrous ether and treated with oxalic acid to provide 11-cyano-11-[3-(1-pyrrolidino)propyl-6,11-dihydrodibenz[b,e]oxepin oxalate. Recrystallization from methanol-ether (1:2) yields colorless crystals, m.p. 161°–163° C. A yield of 37% is obtained upon a second run which is conducted at the temperature of 70°–74° C. for 2½ hours.

ANALYSIS: Calculated for $C_{24}H_{26}N_2O_5$: 68.23%C; 6.20%H; 6.63%N. Found: 68.45%C; 6.18%H; 6.81%N.

EXAMPLE 15

11-Cyano-11-[2-(1-pyrrolidino)propyl]-6,11-dihydrodibenz[b,e]oxepin oxalate

To 4.00 g (0.018 mole) of 11-cyano-6,11-dihydrodibenz[b,e]oxepin of Example 1A in 70 ml of dry dimethylformamide is added at 3°–5° C. 0.50 g (0.022 mole) of 99% sodium hydride and the mixture stirred 30 minutes at 5° C. and one hour at ambient temperature until gas evolution ceases. The mixture is cooled to 5° C. and 3.00 g (0.020 mole) of 2-(1-pyrrolidino)propyl chloride in 20 ml of dry dimethylformamide is quickly added. After heating at 65°–70° C. for 3 hours, the reaction mixture is decanted into 1 liter of ice water and the gum collected by filtration. This crude product is dissolved in ether and extracted with 2 N hydrochloric acid. Basification with $K_2CO_3$ provides a gum which is extracted with ether, dried ($K_2CO_3$), filtered, and concentrated in vacuo to an oil. The oil is dissolved in dry ether and treated with oxalic acid to form the oxalate. Recrystallization from methanol-ether followed by a recrystallization from acetonitrile provides 0.20 g of crystals of 11-cyano-11[2-(1-pyrrolidino)propyl]-6,11-dihydrodibenz[b,e]oxepin oxalate, m.p. 158°–161° C. A yield of 11% is obtained.

ANALYSIS: Calculated for $C_{24}H_{26}N_2O_5$: 68.23%C; 6.20%H; 6.63%N. Found: 68.03%C; 6.23%H; 6.74%N.

EXAMPLE 16

A. 11-Cyano,5,6-dihydro-5-methyl-6-morphanthridone

A mixture of 8.00 g (0.03 mole) of 11-formyl-5,6-dihydro-5-methyl-6-morphanthridone, 2.80 g (0.04 mole) of hydroxylamine hydrochloride, 30 ml of dry pyridine and 122 ml of absolute ethanol is refluxed for 3½ hours and concentrated in vacuo to an oil. The oil is dissolved in dichloromethane, washed with 10% hydrochloric acid, water, dried ($Na_2SO_4$), filtered and concentrated to a solid which is refluxed with 160 ml of acetic anhydride for 4½ hours. The solution is concentrated to an oil which is dissolved in dichloromethane and washed with 5% sodium carbonate, water, and dried ($Na_2SO_4$). Filtration and concentration in vacuo provides crystals which are recrystallized from benzene to yield 4.0 g (50%) of crystals of 11-cyano-5,6-dihydro-5-methyl-6-morphanthridone, m.p. 170°–172° C.

B. 11-Cyano-5,6-dihydro-5-methyl-11-[2-(dimethylamino)ethyl]-6-morphanthridone

To 5.00 g (0.02 mole) of 11-cyano-5,6-dihydro-5-methyl-6-morphanthridone of Example 16A in 25 ml of dry dimethylformamide is added at 5°–10° C., 0.55 g (0.024 mole) of 99% sodium hydride. After 1 hour, the solution is cooled to 5°–10° C. again and 2.16 g (0.022 mole) of 2-dimethylaminoethyl chloride in 10 ml of dry dimethylformamide is added. The solution is stirred for 16 hours at room temperature, at 80° C. for ½ hour and at 50° C. for 1 hour. After decanting the resultant mixture into 1 liter of ice water, the resultant suspension is extracted with ether and the ether extract back extracted with 2 N hydrochloric acid. Basification of the acid solution with potassium carbonate gives an oil which is extracted with ether, dried ($K_2CO_3$), filtered, and concentrated in vacuo to an oil which crystallizes upon standing. Trituration with anhydrous ether provides 4.20 g (65.5%) of crystals of 11-Cyano-5,6-dihydro-5-methyl-11-[2-(dimethylamino)ethyl]-6-morphanthridone, m.p. 116°–118° C.

ANALYSIS: Calculated for $C_{20}H_{21}N_3O$: 75.21%C; 6.63%H; 13.16%N. Found: 75.36%C; 6.65%H; 13.42%N.

EXAMPLE 17

11-Cyano-5,6-dihydro-5-methyl-11-[2-(1-pyrrolidino)ethyl]-6-morphanthridone

To 5.00 g (0.02 mole) of 11-cyano-5,6-dihydro-5-methyl-6-morphanthridone of Example 16A in 25 ml of dry dimethylformamide is added at 5° C., 0.55 g (0.02 mole) of 99% sodium hydride with stirring under nitrogen. The resultant solution is allowed to come to room temperature and stirred for 1½ hours (cessation of gas evolution). After cooling to 5° C., 2.68 g (0.02 mole) of N-(2-chloroethyl)pyrrolidine in 10 ml dry dimethyl formamide is added dropwise. Upon completion of the addition, the mixture is stirred for 16 hours at room temperature and then for 1 hour at 85° C. Following this, the resultant suspension is decanted into 1 liter of ice water and extracted with ether. Extraction of the ether with 2 N hydrochloric acid followed by basification of the acid solution with potassium carbonate (ice cooling) provides a gum which is then extracted with ether. Drying ($K_2CO_3$), filtration, and concentration in vacuo gives a gum which crystallizes. Trituration with ether followed by recrystallization from acetonitrile provides 2.20 g (32%) of crystals of 11-cyano-5,6-dihydro-5-methyl-11-[2-(1-pyrrolidino)ethyl]-6-morphanthridone, m.p. 116°–120° C.

ANALYSIS: Calculated for $C_{22}H_{23}N_3O$: 76.49%C; 6.71%H; 12.17%N. Found: 76.47%C; 6.82%H; 12.28%N.

EXAMPLE 18

11-Cyano-5,6-dihydro-5-methyl-11-[2-(1-piperidino)ethyl]-6-morphanthridone

To 5.00 g (0.02 mole) of 11-cyano-5,6-dihydro-5-methyl-6-morphanthridone of Example 16A in 25 ml of dry dimethylformamide is added at 5°–10° C., 0.55 g (0.02 mole) of 99% sodium hydride. After allowing the mixture to come to room temperature, stirring is continued for 1 hour until cessation of gas evolution. The resultant mixture is cooled to 5° C. and 3.00 g (0.02 mole) of N-(2-chloroethyl)piperidine in 10 ml of dry dimethylformamide is slowly added. After stirring at room temperature for 16 hours, and then at 80° C. for ½ hour and at 55° C. for 1½ hours, the resultant mixture is decanted into 1 liter of ice water and extracted with ether. Extraction of the ether with 2 N hydrochloric acid followed by basification of the ice cold acid extract with potassium carbonate provides a gum which is extracted with ether, dried ($K_2CO_3$), filtered and concentrated in vacuo to a solid which upon trituration with ether gives a colorless solid. Recrystallization from acetonitrile yields 3.8 g (53%) of crystals of 11-cyano-5,6-dihydro-5-methyl-11-[2-(1-piperidino)ethyl]-6-morphanthridone, m.p. 135°–137° C.

ANALYSIS Calculated for $C_{23}H_{25}N_3O$: 76.85%C; 7.02%H; 11.69%N. Found: 76.92%C; 7.07%H; 11.74%N.

EXAMPLE 19

11-Cyano-5,6-dihydro-5-methyl-11-[2-(1-morpholino)ethyl]-6-morphanthridone

To 5.00 g (0.02 mole) of 11-cyano-5,6-dihydro-5-methyl-6-morphanthridone of Example 16A in 25 ml of dry dimethylformamide is added at 5°–10° C., 0.55 g (0.02 mole) of 99% sodium hydride. After the addition, the resultant reaction mixture is stirred at room temperature for 1½ hours and then cooled to 5° C.; 3.00 g (0.02 mole) of N-(2-chloroethyl)morpholine in 10 ml of dry dimethylformamide is added and the mixture then stirred at room temperature for 16 hours, at 80° C. for ½ hour and at 55° C. for 1½ hours. The resultant suspension is decanted into 1 liter of ice water and extracted with ether. Extraction of the ether phase with 2 N hydrochloric acid followed by basification with potassium carbonate (ice added) gives a gum which is extracted with ether. Drying ($K_2CO_3$), filtration and concentration in vacuo yields a solid which is triturated with ether and then recrystallized from acetonitrile to provide 2.80 g (39%) of crystals of 11-cyano-5,6-dihydro-5-methyl-11-[2-(1-morpholino)ethyl]-6-morphanthridone, m.p. 156°–159° C.

ANALYSIS: Calculated for $C_{22}H_{23}N_3O_2$: 73.11%C; 6.41%H; 11.63%N. Found: 73.14%C; 6.38%H; 11.68%N.

EXAMPLE 20

11-Cyano-5,6-dihydro-5-methyl-11-[3-(dimethylamino)propyl]-6-morphanthridone

To 5.00 g (0.02 mole) of 11-cyano-5,6-dihyro-5-methyl-6-morphanthridone of Example 16A in 15 ml of dry dimethylformamide at 5°–7° C. under nitrogen is added 0.55 g (0.02 mole) of 99% sodium hydride and the resultant suspension is stirred at room temperature for 1½ hours until gas evolution ceases. The mixture is cooled to 5° C. and 2.44 g (0.02 mole) of dimethylaminopropyl chloride in 10 ml dry dimethylformamide is added. The mixture is stirred at room temperature for 72 hours, at 95° C. for 1½ hours, and then at 56° C. for 2 hours. After decanting into 1 liter of ice water, the resultant gum is extracted with ether and the ether phase is then extracted with 2 N hydrochloric acid. Basification of the aqueous layer provides a gum which is extracted with ether, dried ($K_2CO_3$), filtered, and concentrated in vacuo to a solid. Recrystallization from acetonitrile provides 1.6 g (24%) of crystals of 11-Cyano-5,6-dihydro-5-methyl-11-[3-(dimethylamino)propyl]-6-morphanthridone, m.p. 96°–98° C.

ANALYSIS: Calculated for $C_{21}H_{23}N_3O$: 75.67%C; 6.95%H; 12.60%N. Found: 75.67%C; 7.08%H; 12.75%N.

EXAMPLE 21

11-Cyano-5,6-dihydro-5-methyl-11-[3-(1-piperidino)propyl]-6-morphanthridone

To 5.00 g (0.02 mole) of 11-cyano-5,6-dihydro-5-methyl-6-morphanthridone of Example 16A in 25 ml of dry dimethylformamide is added under a nitrogen atmosphere at 5°–10° C., 0.55 g (0.02 mole) of 99% sodium hydride. Upon completion of the addition, the resultant solution is allowed to come to room temperature and stirred for 1½ hours until gas evolution ceases. The mixture is cooled to 5° C. and 3.24 g (0.02 mole) of N-(3-chloropropyl)piperidine in 10 ml of dry dimethylformamide is added. After stirring at room temperature for 16 hours, the resultant mixture is stirred at 80° C. for 1½ hours and then at 55° C. for 1½ hours. The mixture is decanted into 1 liter of ice water and then extracted with ether. After extracting the ether phase with 2 N hydrochloric acid and basifying the aqueous layer with potassium carbonate (ice added), the resultant gum is extracted with ether, dried ($K_2CO_3$), filtered and concentrated in vacuo to a solid which is recrystallized twice from acetonitrile to provide 3.3 g (43.5%) of crystals of 11-cyano-5,6-dihydro-5-methyl-11-[3-(1-piperidino)propyl]-6-morphanthridone, m.p. 106°–108° C.

ANALYSIS: Calculated for $C_{24}H_{27}N_3O$: 77.18%C; 7.29%H; 11.25%N. Found: 77.19%C; 7.27%H; 11.34%N.

EXAMPLE 22

11-Cyano-5,6-dihydro-5-methyl-11-[2-(dimethylamino)ethyl]-6-morphanthridone

To 5.00 g (0.02 mole) of 11-cyano-5,6-dihydro-5-methyl-6-morphanthridone of Example 16A in 25 ml of dry dimethylformamide at 5°–10° C. is added 0.55 g (0.02 mole) of 99% sodium hydride. The resultant solution is stirred at room temperature for 1½ hours and then cooled to 7° C. and 2.72 g (0.02 mole) of diethylaminoethyl chloride in 10 ml of dry dimethylformamide is added. The reaction mixture is stirred at room temperature for 18 hours, at 85° C. for 1½ hours, and at 50° C. for one hour. After decanting the reaction mixture into 1 liter of ice water, the resulting gum is extracted with ether and then the ether phase back extracted with 2 N hydrochloric acid. Basification of the aqueous layer with potassium carbonate (ice cooling) provides a gum which is extracted with ether. Drying ($K_2CO_3$), filtration, and concentration in vacuo yields a gum which solidifies upon standing. Recrystallization from acetonitrile provides 4.40 g (63%) of colorless crystals of 11-Cyano-5,6-dihydro-5-methyl-11-[2-(dimethylamino)ethyl]-6-morphanthridone, m.p. 94°–96° C.

ANALYSIS: Calculated for $C_{22}H_{25}N_3O$: 76.05%C; 7.25%H; 12.09%N. Found: 76.31%C; 7.45%H; 12.39%N.

EXAMPLE 23

11-Cyano-5,6-dihydro-5-methyl-11-[3-(diethylamino)propyl]-6-morphanthridone oxalate To 5.00 g (0.02 mole) of 11-cyano-5,6-dihydro-5-methyl-6-morphanthridone of Example 16A in 25 ml of dry dimethylformamide at 5°–10° C. is added with stirring 0.55 g (0.022 mole) of 99% sodium hydride. After gas evolution ceases, the resultant solution is stirred at room temperature for one-half hour and then cooled to 7° C.; 3.56 g (0.02 mole) of 3-diethylaminopropyl chloride in 10 ml dry dimethylformamide is then added. The mixture is stirred at room temperature for 16 hours, at 80° C. for ½ hour, and at 55° C. for 1½ hours and then decanted into ice water. The resultant gum is extracted with ether and the combined ether extracts back extracted with 2 N hydrochloric acid. Basification (ice cooling) with potassium carbonate followed by extraction with ether gives a solution which is dried ($K_2CO_3$), filtered, and concentrated in vacuo to an oil which is dissolved in ether and treated with oxalic acid to provide 3.60 g of crystals of the oxalate which upon recrystallization from ether-methanol (1:2) yields 3.00 g (36%) of crystals of 11-Cyano-5,6-dihydro-5-methyl-11-[3-

(diethylamino)propyl]-6-morphanthridone oxalate, m.p. 195°–196° C.

ANALYSIS: Calculated for $C_{25}H_{29}N_3O_5$: 66.50%C; 6.47%H; 9.31%N. Found: 66.48%C; 6.48%H; 9.37%N.

EXAMPLE 24

A.

11-Chloro-2-methoxy-6,11-dihydrodibenz[b,e]oxepin

11-Hydroxy-2-methoxy-6,11-dihydrodibenz[b,e]oxepin (13.85 g, 0.057 mole) is dissolved in anhydrous ether (180 ml) and cooled to 5° C. under a dry nitrogen atmosphere. Thionyl chloride (7.37 g; 0.062 mole) in ether (20 ml) is added dropwise while maintaining the temperature below 5° C. (Near the end of the addition a solid precipitates from the solution). The reaction is stirred at ambient temperature for 3 hours and filtered. The filtrate is removed in vacuo to give a solid which is combined with the filtered solid and recrystallized from cyclohexane to provide 10.5 g (70%) of crystals of 11-chloro-2-methoxy-6,11-dihydrodibenz[b,e]oxepin, m.p. 133°–134.5° C.

ANALYSIS: Calculated for $C_{15}H_{13}ClO_2$: 69.10%C; 5.02%H; 13.60%Cl. Found: 69.01%C; 5.15%H; 13.33%Cl.

B. 11-Cyano-2-methoxy-6,11-dihydrodibenz[b,e]oxepin

11-Chloro-2-methoxy-6,11-dihydrodibenz[b,e]oxepin (10.1 g; 0.038 mole) of Example 24A is dissolved in dry benzene (170 ml) and placed under a dry nitrogen atmosphere. To this solution is added in one portion, CuCN (8.5 g; 0.095 mole). The reaction is brought to reflux (twenty minutes), filtered while hot and the salts are washed with benzene. Removal of the solvent in vacuo yields an oil. The oil is dissolved in a minimal amount of benzene and hexane is added with cooling. The resulting solid is filtered and recrystallized from ethanol to give a solid of 11-cyano-2-methoxy-6,11-dihydrodibenz[b,e]oxepin, m.p. 120°–122° C.

ANALYSIS: Calculated for $C_{16}H_{13}NO_2$: 76.47%C; 5.21%H. Found: 76.42%C; 5.24%H.

The resultant compound may be reacted in a similar manner, described below for Example 25C, to yield 11-cyano-2-methoxy-11-[3-(dimethylamino)propyl]-6,11-dihydrodibenz[b,e]oxepin.

EXAMPLE 25

A. 2,11-Dichloro-6,11-dihydrodibenz[b,e]oxepin

2-Chloro-11-hydroxy-6,11-dihydrodibenz[b,e]oxepin (12.75 g; 0.051 mole) is dissolved in dry ether (220 ml) and cooled to 5° C. under a dry nitrogen atmosphere. Thionyl chloride (6.76 g; 0.056 mole) in ether (20 ml) is slowly added dropwise while maintaining the temperature below 5° C. Upon completion of the addition, the reaction is brought to ambient temperature and stirred for three hours. Upon removal of the solvent in vacuo, the resulting solid is recrystallized from cyclohexane to give crystals of 2,11-dichloro-6,11-dihydrodibenz[b,e]oxepin, m.p. 125°–127° C.

ANALYSIS: Calculated for $C_{14}H_{10}Cl_2O$: 63.42%C; 3.80%H; 26.75%Cl. Found: 63.91%C; 3.84%H; 26.98%Cl.

B. 2-Chloro-11-cyano-6,11-dihydrodibenz[b,e]oxepin 2,11-Dichloro-6,11-dihydrodibenz[b,e]oxepin (7.7 g; 0.03 mole) of example 25-A is dissolved in dry toluene (120 ml) and placed under a positive dry nitrogen atmosphere. To this solution is added CuCN (5.2 g; 0.05 mole) in one portion and the reaction brought to reflux for 6½ hours. The reaction mixture is filtered while hot (80° C.) and the salts washed with toluene. After removing the filtrate in vacuo the resulting solid is triturated with hexane and dried to yield 2-chloro-11-cyano-6,11-dihydrodibenz[b,e]oxepin, m.p. 113°–115° C.

ANALYSIS: Calculated for $C_{15}H_{10}ClNO$: 70.45%C; 3.94%H; 13.86%Cl. Found: 70.48%C; 4.14%H; 13.85%Cl.

C.

2-Chloro-11-cyano-11-[3-(dimethylamino)propyl]-6,11-dihydrodibenz[b,e]oxepin hydrochloride 2-Chloro-11-cyano-6,11-dihydrodibenz[b,e]oxepin (4.6 g; 0.017 mole) of Example 25B is dissolved in dry dimethylformamide (DMF) [40 ml] under nitrogen and cooled to 5° C. Sodium hydride (99%) (0.45 g; 0.018 mole) is added in one portion and stirred for five minutes. It is then brought to ambient temperature and stirred for thirty minutes. After cooling to 3° C. 3-dimethylaminopropyl chloride (2.18 g; 0.018 mole) in dry DMF (20 ml) is added dropwise. Upon completion of the addition, the reaction mixture is brought to ambient temperature for thirty minutes and then heated at 60° C. for eight hours. The reaction mixture is cooled and poured with stirring into 600 ml ice water. The resulting solid is filtered, dissolved in ether and extracted with 2 N HCl. The acidic aqueous portion is basified with 10% NaOH and the precipitate filtered and dried. The solid is dissolved in ether and treated with ethereal HCl. After filtering, the solid is washed with ether and dried. Recrystallization from acetonitrile provides 1.0 g (16%) of crystals of 2-chloro-11-cyano-11-[3(dimethylamino)propyl]-6,11-dihydrodibenz[b,e]oxepin hydrochloride, m.p. 217°–219° C.

ANALYSIS: Calculated for $C_{20}H_{22}Cl_2N_2O$: 63.66%C; 5.88%H; 7.43%N. Found: 63.75%C; 6.00%H; 7.40%N.

EXAMPLE 26

A. 8,11-Dichloro-6,11-dihydrodibenz[b,e,]oxepin

To 5.50 g (0.024 mole) of 8-chloro-11-hydroxy-6,11-dihydrodibenz[b,e]oxepin in 95 ml of dry ether is added dropwise at 5°–10° C. 3.00 g (0.025 mole) of thionyl chloride in 10 ml of dry ether. The solution is stirred at ambient temperature for 3 hours and then concentrated in vacuo to a solid. Recrystallization of the solid from acetonitrile followed by a second recrystallizaton from hexane provides 4.0 g (63%) of crystals of 8,11-dichloro-6,11-dihydrodibenz[b,e]oxepin, m.p. 108°–111° C.

ANALYSIS: Calculated for $C_{14}H_{10}Cl_2O$: 63.42%C; 3.80%H. Found: 64.03%C; 3.80%H.

B. 8-Chloro-11-cyano-6,11-dihydrodibenz[b,e]oxepin

To 3.20 g of 8,11-dichloro-6,11-dihydrodibenz[b,e]oxepin of Example 26A, in 80 ml of dry toluene is added 2.3 g of CuCN and the resultant suspension is refluxed for 7 hours and then filtered. Concentration in vacuo of the resultant filtrate provides a solid which upon trituration with acetonitrile yields 2.3 g of crystals of 8-chloro-11-cyano-6,11-dihydrodibenz [b,e]oxepin m.p. 124°–128° C.

C.
8-Chloro-11-cyano-11-[3-(dimethylamino)propyl]-6,11-dihydrodibenz[b,e]oxepin oxalate To 11.5 g (0.045 mole) of 8-chloro-11-cyano-6,11-dihydrodibenz[b,e]oxepin of Example 26B in 300 ml of dry DMF at 0°-2° C. is added 1.25 g (0.054 mole) of 99% sodium hydride and the mixture is stirred at 0° C. for 15 minutes and then at ambient temperature for one hour. The resultant suspension is cooled to 2° C. and 6.10 g (0.05 mole) of 3-dimethylaminopropyl chloride in 20 ml of dry DMF is added. After heating at 68°-70° C. for 4 hours, the mixture is decanted back into 1 liter of ice water and extracted with ether. The combined ether extracts are back extracted with 2 N hydrochloric acid and the aqueous phase is basified (ice cooled) with potassium carbonate. The resulting gum is extracted with ether, dried (Na$_2$SO$_4$), filtered, and concentrated in vacuo to an oil. Treatment of the oil in dry ether with oxalic acid provides the oxalate salt which is recrystallized from methanol-ether and then acetonitrile to yield 1.60 g of crystals of 8-chloro-11-cyano-11-[3-(dimethylamino)propyl]-6,11-dihydrodibenz[b,e]oxepin oxalate.

ANALYSIS: Calculated for C$_{22}$H$_{23}$ClN$_2$O$_5$: 61.32%C; 5.37%H; 6.50%N. Found: 61.06%C; 5.24%H; 6.46%N.

EXAMPLE 27

A. 11-Chloro-6,11-dihydrodibenz[b,e]thiepin

A solution of 33 g of 11-hydroxy-6,11-dihydrodibenz[b,e]thiepin in 400 ml of absolute alcohol is saturated with hydrogen chloride gas at 5° C. for ½ hour. The resulting solution is dried with CaCl$_2$, filtered and concentrated in vacuo to an oil which crystallizes upon standing in a refrigerator (10° C.) after 3 days. Recrystallization from cyclohexane provides 27 g of 11-chloro-6,11-dihydrodibenz[b,e]thiepin m.p. 79°-82° C.

B. 11-Cyano-6,11-dihydrodibenz[b,e]thiepin

To 23.3 g of 11-chloro-6,11-dihydrodibenz[b,e]thiepin of Example 27A, in 583 ml of dry benzene is added 21 g of CuCN and the resultant suspension is refluxed for 4 hours. The resultant reaction mixture is hot filtered and the solid material is washed with benzene. Concentration of the resultant filtrate in vacuo provides an oil which upon treatment with ethanol yields 4.0 g of 11-cyano-6,11-dihydrodibenz[b,e]thiepin, m.p. 128° C.-130° C.

C. 11-Cyano-11-[3-(dimethylamino)propyl]-6,11-dihydrodibenz[b,e]thiepin hydrochloride To 3.30 g (0.014 mole) of 11-cyano-6,11-dihydrodibenz[b,e]thiepin of Example 27B in 140 ml of dry DMF is added at 0° C. 0.41 g (0.017 mole) of 99% sodium hydride. After 2 hours at ambient temperature, the resultant solution is cooled to 0° C. and 1.71 g (0.014 mole) of 3-dimethylaminopropyl chloride in 10 ml of dry DMF is added dropwise. The resultant reaction mixture is heated at 65° C. for 2 hours and then at 75° C. for 4 hours and decanted into 1 liter of ice water. The crude product is extracted with ether and back extracted with 2 N hydrochloric acid. Basification with 10% sodium hydroxide (ice cooling) yields a gum which is extracted with ether, dried (K$_2$CO$_3$), filtered and concentrated in vacuo to an oil. After dissolving the oil in dry ether, HCl gas is added and the resulting gum is washed with ether and then is recrystallized from methanol ether. Recrystallization from acetonitrile provides 0.45 g (10%) of crystals of 11-cyano-11-[3-(dimethylamino)propyl]-6,11-dihydrodibenz[b,e]thiepin hydrochloride, m.p. 214°-216° C.

ANALYSIS: Calculated for C$_{20}$H$_{23}$N$_3$SCl: 66.92%C; 6.46%H; 7.81%N. Found: 66.46%C; 6.54%H; 7.95%N.

We claim:

1. A compound depicted by the formula,

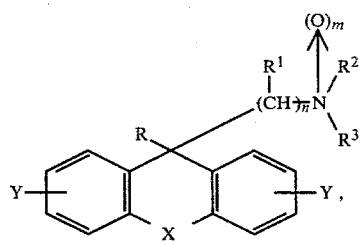

where R is selected from

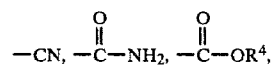
$-CN$, $-\overset{O}{\underset{\|}{C}}-NH_2$, $-\overset{O}{\underset{\|}{C}}-OR^4$, where $R^4$ is selected from H or alkyl; $R^1$ is hydrogen or alkyl; $R^2$ and $R^3$ are the same or different and are selected from H, and alkyl or $R^2$ and $R^3$ are fused to form the pyrrolidinyl, morpholino, piperidinyl and azepinyl group; Y is selected from H, halogen and alkoxy; X is selected from

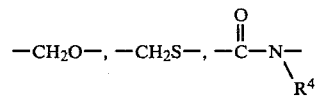
$-CH_2O-$, $-CH_2S-$, $-\overset{O}{\underset{\|}{C}}-\underset{\underset{R^4}{\diagdown}}{N}-$ where $R^4$ is as defined above; m is an integer of 0 or 1 and n is an integer of 2 or 3, and the pharmaceutically acceptable salts thereof.

2. The compound as defined in claim 1 wherein X is $-CH_2O-$.

3. The compound as defined in claim 2 which is 11-cyano-11-[2-(dimethylamino)ethyl]-6,11-dihydrodibenz[b,e]oxepin or the pharmaceutically acceptable salt thereof.

4. The compound as defined in claim 2 which is 11-cyano-11-[2-(1-piperidino)ethyl]-6,11-dihydrodibenz[b,e]oxepin or the pharmaceutically acceptable salt thereof.

5. The compound as defined in claim 2 which is 11-cyano-11-[2-(1-morpholino)ethyl]-6,11-dihydrodibenz[b,e]oxepin or the pharmaceutically acceptable salt thereof.

6. The compound as defined in claim 2 which is 11-cyano-11-[3-(dimethylamino)propyl]-6,11-dihydrodibenz[b,e]oxepin or the pharmaceutically acceptable salt thereof.

7. The compound as defined in claim 2 which is 11-cyano-11-[2-(methylamino)ethyl]-6,11-dihydrodibenz[b,e]oxepin or the pharmaceutically acceptable salt thereof.

8. The compound as defined in claim 2 which is 11-carbamoyl-11-[3-(dimethylamino)propyl]-6,11-dihydrodibenz[b,e]oxepin or the pharmaceutically acceptable salt thereof.

9. The compound as defined in claim 2 which is 11-cyano-11-[3-(di-methylamino)propyl]-6,11-dihydrodibenz[b,e]oxepin-N-oxide or the pharmaceutically acceptable salt thereof.

10. The compound as defined in claim 2 which is 11-cyano-11-[2-(1-pyrrolidino)ethyl]-6,11-dihydrodibenz[b,e]oxepin or the pharmaceutically acceptable salt thereof.

11. The compound as defined in claim 2 which is 11-cyano-11-[3-(1-piperidino)propyl]-6,11-dihydrodibenz[b,e]oxepin or the pharmaceutically acceptable salt thereof.

12. The compound as defined in claim 2 which is 11-cyano-11-[2-(diethylamino)ethyl]-6,11-dihydrodibenz[b,e]oxepin or the pharmaceutically acceptable salt thereof.

13. The compound as defined in claim 2 which is 11-cyano-11-[2-(hexamethylene imino)ethyl]-6,11-dihydrodibenz[b,e]oxepin or the pharmaceutically acceptable salt thereof.

14. The compound as defined in claim 2 which is 11-cyano-11-[3-(diethylamino)propyl]-6,11-dihydrodibenz[b,e]oxepin or the pharmaceutically acceptable salt thereof.

15. The compound as defined in claim 2 which is 11-cyano-11-[3-(1-pyrrolidino)propyl]-6,11-dihydrodibenz[b,e]oxepin or the pharmaceutically acceptable salt thereof.

16. The compound as defined in claim 2 which is 11-cyano-11-[2-(1-pyrrolidino)propyl]-6,11-dihydrodibenz[b,e]oxepin or the pharmaceutically acceptable salt thereof.

17. The compound as defined in claim 2 which is 2-chloro-11-cyano-11-[3-(dimethylamino)propyl]-6,11-dihydrodibenz[b,e]oxepin or the pharmaceutically acceptable salt thereof.

18. The compound as defined in claim 2 which is 8-chloro-11-cyano-11-[3-(dimethylamino)propyl]-6,11-dihydrodibenz[b,e]oxepin or the pharmaceutically acceptable salt thereof.

19. The compound as defined in claim 1 wherein X is

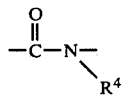

20. The compound as defined in claim 19 which is 11-cyano-5,6-dihydro-5-methyl-11-[2-(dimethylamino)ethyl]-6-morphanthridone or the pharmaceutically acceptable salt thereof.

21. The compound as defined in claim 19 which is 11-cyano-5,6-dihydro-5-methyl-11-[2-(1-pyrrolidino)ethyl]-6-morphanthridone or the pharmaceutically acceptable salt thereof.

22. The compound as defined in claim 19 which is 11-cyano-5,6-dihydro-5-methyl-11-[2-(1-piperidino)ethyl]-6-morphanthridone or the pharmaceutically acceptable salt thereof.

23. The compound as defined in claim 19 which is 11-cyano-5,6-dihydro-5-methyl-11-[2-(1-morpholino)ethyl]-6-morphanthridone or the pharmaceutically acceptable salt thereof.

24. The compound as defined in claim 19 which is 11-cyano-5,6-dihydro-5-methyl-11-[3-(dimethylamino)propyl]-6-morphanthridone or the pharmaceutically acceptable salt thereof.

25. The compound as defined in claim 19 which is 11-cyano-5,6-dihydro-5-methyl-11-[3-(1-piperidino)propyl]-6-morphanthridone or the pharmaceutically acceptable salt thereof.

26. The compound as defined in claim 19 which is 11-cyano-5,6-dihydro-5-methyl-11-[2-(dimethylamino)ethyl]-6-morphanthridone or the pharmaceutically acceptable salt thereof.

27. The compound as defined in claim 19 which is 11-cyano-5,6-dihydro-5-methyl-11-[3-(dimethylamino)propyl]-6-morphanthridone or the pharmaceutically acceptable salt thereof.

28. The compound as defined in claim 1 wherein X is $-CH_2S-$.

29. The compound as defined in claim 28 which comprises 11-cyano-11-[3-(dimethylamino)propyl]-6,11-dihydrodibenz[b,e]thiepin or the pharmaceutically acceptable salt thereof.

30. A diuretic composition which comprises a diuretically effective amount of a compound

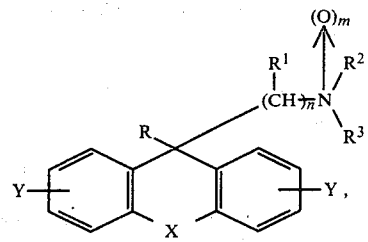

where R is selected from

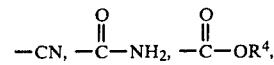

where $R^4$ is selected from H, and alkyl; $R^1$ is selected from H and alkyl; $R^2$ and $R^3$ are the same or different and are selected from H and alkyl or $R^2$ and $R^3$ are fused to form the pyrrolidinyl, morpholino, piperidinyl and azepinyl ring substituent; Y is selected from H, halogen and alkoxy; X is selected from

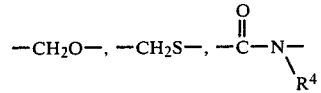

where $R^4$ is as defined above; m is an integer of 0 or 1; and n is an integer of 2 or 3, and the pharmaceutically acceptable salts thereof.

31. The composition as defined in claim 30 wherein X of said compound is $-CH_2O-$.

32. The composition as defined in claim 31 which comprises 11-cyano-11-[2-(dimethylamino)ethyl]-6,11-dihydrodibenz[b,e]oxepin or the pharmaceutically acceptable salt thereof.

33. The composition as defined in claim 31 which comprises 11-cyano-11-[2-(1-piperidino)ethyl]-6,11-dihydrodibenz[b,e]oxepin or the pharmaceutically acceptable salt thereof.

34. The composition as defined in claim 31 which comprises 11-cyano-11-[2-(1-morpholino)ethyl]-6,11- dihydrodibenz[b,e]oxepin or the pharmaceutically acceptable salt thereof.

35. The composition as defined in claim 31 which comprises 11-cyano-11-[3-(dimethylamino)propyl]-6,11-dihydrodibenz[b,e]oxepin or the pharmaceutically acceptable salt thereof.

36. The composition as defined in claim 31 which comprises 11-cyano-11-[2-(methylamino)ethyl]-6,11-dihydrodibenz[b,e]oxepin or the pharmaceutically acceptable salt thereof.

37. The composition as defined in claim 31 which comprises 11-carbamoyl-11-[3-(dimethylamino)propyl]-6,11-dihydrodibenz[b,e]oxepin or the pharmaceutically acceptable salt thereof.

38. The composition as defined in claim 31 which comprises 11-cyano-11-[3-(dimethylamino)propyl]-6,11-dihydrodibenz[b,e]oxepin-N-oxide or the pharmaceutically acceptable salt thereof.

39. The composition as defined in claim 31 which comprises 11-cyano-11-[2-(1-pyrrolidino)ethyl]-6,11-dihydrodibenz[b,e]oxepin or the pharmaceutically acceptable salt thereof.

40. The composition as defined in claim 31 which comprises 11-cyano-11-[3-(1-piperidino)propyl]-6,11-dihydrodibenz[b,e]oxepin or the pharmaceutically acceptable salt thereof.

41. The composition as defined in claim 31 which comprises 11-cyano-11-[2-(diethylamino)ethyl]-6,11-dihydrodibenz[b,e]oxepin or the pharmaceutically acceptable salt thereof.

42. The composition as defined in claim 31 which comprises 11-cyano-11-[2-(hexamethylene imino)ethyl]-6,11-dihydrodibenz[b,e]oxepin or the pharmaceutically acceptable salt thereof.

43. The composition as defined in claim 31 which comprises 11-cyano-11-[3-(diethylamino)propyl]-6,11-dihydrodibenz[b,e]oxepin or the pharmaceutically acceptable salt thereof.

44. The composition as defined in claim 31 which comprises 11-cyano-11-[3-(1-pyrrolidino)propyl]-6,11-dihydrodibenz[b,e]oxepin or the pharmaceutically acceptable salt thereof.

45. The composition as defined in claim 31 which comprises 11-cyano-11-[2-(1-pyrrolidino)propyl]-6,11-dihydrodibenz[b,e]oxepin or the pharmaceutically acceptable salt thereof.

46. The composition as defined in claim 31 which comprises 2-chloro-11-cyano-11-[3-dimethylamino)propyl]-6,11-dihydrodibenz[b,e]oxepin or the pharmaceutically acceptable salt thereof.

47. The composition as defined in claim 31 which comprises 8-chloro-11-cyano-11-[3-(dimethylamino)propyl]-6,11-dihydrodibenz[b,e]oxepin or the pharmaceutically acceptable salt thereof.

48. The composition as defined in claim 30 comprising said compound wherein X is

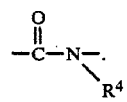

49. The composition as defined in claim 48 which comprises 11-cyano-5,6-dihydro-5-methyl-11-[3-(diethylamino)propyl]-6-morphanthridone or the pharmaceutically acceptable salt thereof.

50. The composition as defined in claim 48 which comprises 11-cyano-5,6-dihydro-5-methyl-11-[2-(dimethylamino)ethyl]-6-morphanthridone or the pharmaceutically acceptable salt thereof.

51. The composition as defined in claim 48 which comprises 11-cyano-5,6-dihydro-5-methyl-11-[2-(1-pyrrolidino)ethyl]-6-morphanthridone or the pharmaceutically acceptable salt thereof.

52. The composition as defined in claim 48 which comprises 11-cyano-5-,6-dihydro-5-methyl-11-[2-(1-piperidino)ethyl]-6-morphanthridone or the pharmaceutically acceptable salt thereof.

53. The composition as defined in claim 48 which comprises 11-cyano-5,6-dihydro-5-methyl-11-[2-(1-morpholino)ethyl]-6-morphanthridone or the pharmaceutically acceptable salt thereof.

54. The composition as defined in claim 48 which comprises 11-cyano-5,6-dihydro-5-methyl-11-[3-(dimethylamino)propyl]-6-morphanthridone or the pharmaceutically acceptable salt thereof.

55. The composition as defined in claim 48 which comprises 11-cyano-5,6-dihydro-5-methyl-11[3-(1-piperidino)propyl]-6-morphanthridone or the pharmaceutically acceptable salt thereof.

56. The composition as defined in claim 48 which comprises 11-cyano-5,6-dihydro-5-methyl-11-[(2-diethylamino)-ethyl]-6-morphanthridone or the pharmaceutically acceptable salt thereof.

57. The composition as defined in claim 30 comprising said compound wherein X is —CH₂S—.

58. The composition as defined in claim 57 wherein said compound is 11-cyano-11-[3-(dimethylamino)propyl]-6,11-dihydrodibenz[b,e]thiepin or the pharmaceutically acceptable salt thereof.

59. A method of producing diuresis which comprises administering to a mammal a diuretically effective amount of a compound depicted by the formula,

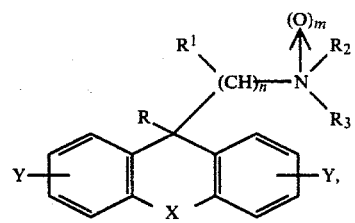

where R is selected from

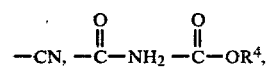

where R⁴ is selected from H and alkyl; R¹ is selected from H and alkyl; R² and R³ are the same or different and are selected from H and alkyl or R² and R³ are fused to form the pyrrolidinyl, morpholino, piperidinyl and azepinyl group; Y is selected from H, halogen and alkoxy; X is selected from

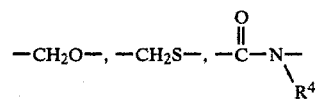

where R⁴ is as defined above; m is an integer selected from 0 and 1; and n is an integer selected from 2 and 3; and the pharmaceutically acceptable salts thereof.

60. The method as defined in claim 59 wherein X of said compound is —CH₂O—.

61. The method as defined in claim 60 wherein said compound is 11-cyano-11-[2-(dimethylamino)ethyl]-6,11-dihydrodibenz[b,e]oxepin or the pharmaceutically acceptable salt thereof.

62. The method as defined in claim 60 wherein said compound is 11-cyano-11-[2-(1-piperidino)ethyl]-6,11-dihydrodibenz[b,e]oxepin or the pharmaceutically acceptable salt thereof.

63. The method as defined in claim 60 wherein said compound is 11-cyano-11-[2-(1-morpholino)ethyl]-6,11-dihydrodibenz[b,e]oxepin or the pharmaceutically acceptable salt thereof.

64. The method as defined in claim 60 wherein said compound is 11-cyano-11-[3-(dimethylamino)propyl]-6,11-dihydrodibenz[b,e]oxepin or the pharmaceutically acceptable salt thereof.

65. The method as defined in claim 60 wherein said compound is 11-cyano-11-[2-(methylamino)ethyl]-6,11-dihydrodibenz[b,e]oxepin or the pharmaceutically acceptable salt thereof.

66. The method as defined in claim 60 wherein said compound is 11-carbamoyl-11-[3-(dimethylamino)propyl]-6,11-dihydrodibenz[b,e]oxepin or the pharmaceutically acceptable salt thereof.

67. The method as defined in claim 60 wherein said compound is 11-cyano-11-[3-(dimethylamino)propyl]-6,11-dihydrodibenz[b,e]oxepin-N-oxide or the pharmaceutically acceptable salt thereof.

68. The method as defined in claim 60 wherein said compound is 11-cyano-11-[2-(1-pyrrolidino)ethyl]-6,11-dihydrodibenz[b,e]oxepin or the pharmaceutically acceptable salt thereof.

69. The method as defined in claim 60 wherein said compound is 11-cyano-11-[3-(1-piperidino)propyl]-6,11-dihydrodibenz[b,e]oxepin or the pharmaceutically acceptable salt thereof.

70. The method as defined in claim 60 wherein said compound is 11-cyano-11-[2-(diethylamino)ethyl]-6,11-dihydrodibenz[b,e]oxepin or the pharmaceutically acceptable salt thereof.

71. The method as defined in claim 60 wherein said compound is 11-cyano-11[2-(hexamethylene imino)ethyl]-6,11-dihydrodibenz[b,e]oxepin or the pharmaceutically acceptable salt thereof.

72. The method as defined in claim 60 wherein said compound is 11-cyano-11-[3-(diethylamino)propyl]-6,11-dihydrodibenz[b,e]oxepin or the pharmaceutically acceptable salt thereof.

73. The method as defined in claim 60 wherein said compound is 11-cyano-11-[3-(1-pyrrolidino)propyl]-6,11-dihydrodibenz[b,e]oxepin or the pharmaceutically acceptable salt thereof.

74. The method as defined in claim 60 wherein said compound is 11-cyano-11-[2-(1-pyrrolidino)propyl]-6,11-dihydrodibenz[b,e]oxepin or the pharmaceutically acceptable salt thereof.

75. The method as defined in claim 60 wherein said compound is 2-chloro-11-cyano-11-[3-(dimethylamino)propyl]-6,11-dihydrodibenz[b,e]oxepin or the pharmaceutically acceptable salt thereof.

76. The method as defined in claim 60 wherein said compound is 8-chloro-11-cyano-11-[3-(dimethylamino)propyl]-6,11-dihydrodibenz[b,e]oxepin or the pharmaceutically acceptable salt thereof.

77. The method as defined in claim 59 wherein the X of said compound is

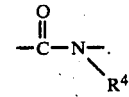

78. The method as defined in claim 77 wherein said compound is 11-cyano-5,6-dihydro-5-methyl-11-[2-(dimethylamino)ethyl]-6-morphanthridone or the pharmaceutically acceptable salt thereof.

79. The method as defined in claim 77 wherein said compound is 11-cyano-5,6-dihydro-5-methyl-11-[2-(1-pyrrolidino)ethyl]-6-morphanthridone or the pharmaceutically acceptable salt thereof.

80. The method as defined in claim 77 wherein said compound is 11-cyano-5,6-dihydro-5-methyl-11-[2-(1-piperidino)ethyl]-6-morphanthridone or the pharmaceutically acceptable salt thereof.

81. The method as defined in claim 77 wherein said compound is 11-cyano-5,6-dihydro-5-methyl-11-[2-(1-morpholinoethyl]-6-morphanthridone or the pharmaceutically acceptable salt thereof.

82. The method as defined in claim 77 wherein said compound is 11-cyano-5,6-dihydro-5-methyl-11-[3-(dimethylamino)propyl]-6-morphanthridone or the pharmaceutically acceptable salt thereof.

83. The method as defined in claim 77 wherein said compound is 11-cyano-5,6-dihydro-5-methyl-11-[3-(1-piperidino)propyl]-6-morphanthridone or the pharmaceutically acceptable salt thereof.

84. The method as defined in claim 77 wherein said compound is 11-cyano-5,6-dihydro-5-methyl-11-[2-(diethylamino)ethyl]-6-morphanthridone or the pharmaceutically acceptable salt thereof.

85. The method as defined in claim 77 wherein said compound is 11-cyano-5,6-dihydro-5-methyl-11-[3-(dimethylamino)propyl]-6-morphanthridone or the pharmaceutically acceptable salt thereof.

86. The method as defined in claim 59 wherein the X of said compound is —CH₂S—.

87. The method as defined in claim 86 wherein said compound is 11-cyano-11-[3-(dimethylamino)propyl]-6,11-dihydrodibenz[b,e]thiepin or the pharmaceutically acceptable salt thereof.

* * * * *

UNITED STATES PATENT AND TRADEMARK OFFICE
CERTIFICATE OF CORRECTION

PATENT NO. : 4,335,122  
DATED : June 15, 1982  
INVENTOR(S) : A. R. McFadden, et al.

Page 1 of 5

It is certified that error appears in the above-identified patent and that said Letters Patent are hereby corrected as shown below:

Column 7, line 23: In the structure of compound (XXII)

"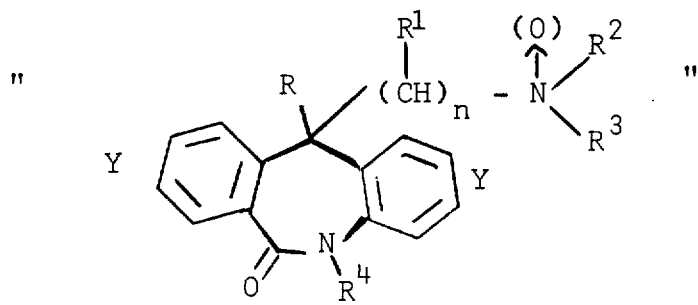"

should be

--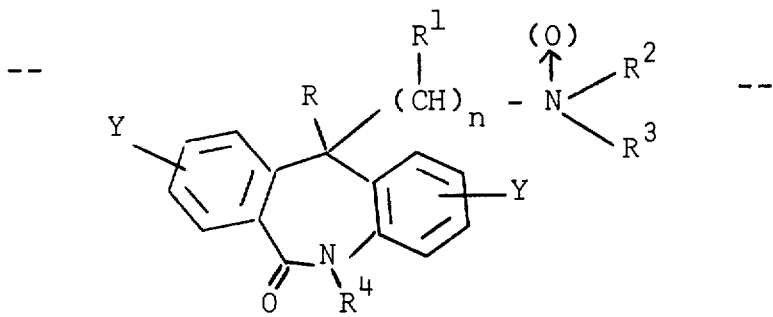--

UNITED STATES PATENT AND TRADEMARK OFFICE
CERTIFICATE OF CORRECTION

PATENT NO. : 4,335,122

DATED : June 15, 1982

INVENTOR(S) : A. R. McFadden, et al.

It is certified that error appears in the above—identified patent and that said Letters Patent is hereby corrected as shown below:

Column 8, Table I: In the second compound
"11-cyano-11[2-(1-..." should be
--11-cyano-11-[2-(1-...--

Column 8, Table I: In the penultimate compound
"11-cyano-5,6-dihydro-5-methyl-
11[3-..." should be
--11-cyano-5,6-dihydro-5-methyl-
11-[3-...--

Column 9, line 33: "11-[2-(butylpentylamino propyl]-..."
should be
--11-[2-butylpentylaminopropyl]-...--

Column 10, line 41: "11-cyano-8-ethoxy-5-methyl-5,6,-..."
should be
--11-cyano-8-ethoxy-5-methyl-5,6-...--

Column 10, line 45: "9-bromo-11-cyano-5-propyl-5,6-dihydro-
11[3-..."
should be
--9-bromo-11-cyano-5-propyl-5,6-dihydro-
11-[3-...--

UNITED STATES PATENT AND TRADEMARK OFFICE
CERTIFICATE OF CORRECTION

PATENT NO. : 4,335,122
DATED : June 15, 1982
INVENTOR(S) : A. R. McFadden, et al.

It is certified that error appears in the above—identified patent and that said Letters Patent is hereby corrected as shown below:

Column 13, line 62: "dimethyl formamide" should be
    --dimethylformamide--
Column 14, line 11: "11-cyano..." should be
    --11-Cyano...--
Column 14, line 28: "combinded" should be
    --combined--
Column 14, line 48: "portion wise" should be
    -- portionwise --
Column 14, line 65: "11-cyano..." should be
    --11-Cyano...--
Column 15, line 10: "2 N" should be
    --2N--
Column 15, line 19: "7.23%;" should be
    --7.23%H;--
Column 16, line 4: "...dibenz[b,e[oxepin..." should be
    --...dibenz[b,e,]oxepin...--
Column 16, line 6: "...cyano6,11-dihydro..." should be
    --...cyano-6,11-dihydro...--

UNITED STATES PATENT AND TRADEMARK OFFICE
CERTIFICATE OF CORRECTION

PATENT NO. : 4,335,122

DATED : June 15, 1982

INVENTOR(S) : A. R. McFadden, et al.

It is certified that error appears in the above—identified patent and that said Letters Patent is hereby corrected as shown below:

Column 17, line 32: "$(C_{23}H_{26}N_2O$:" should be --$C_{23}H_{26}N_2O$:--

Column 17, line 53: "(305)" should be --(30%)--

Column 17, line 62: "11-Cyano-11-[2 (hexa..." should be --11-Cyano-11-[2-(hexa...--

Column 19, line 25: "11-cyano-11[2-..." should be --11-cyano-11-[2-...--

Column 19, line 32: "A. 11-Cyano,5,6-dihydro..." should be -- A. 11-Cyano-5,6-dihydro...--

Column 19, line 68: "11-Cyano..." should be --11-cyano...--

Column 21, line 48: "11-Cyano..." should be --11-cyano...--

Column 22, lines 38 & 39:
  "11-Cyano..." should be --11-cyano...--

Column 22, line 68: "11-Cyano..." should be --11-cyano...--

Column 23, line 65: "example" should be --Example--

Column 24, line 35: "...11-[3(dimethyl..." should be --...11-[3-(dimethyl...--

UNITED STATES PATENT AND TRADEMARK OFFICE
CERTIFICATE OF CORRECTION

PATENT NO. : 4,335,122

DATED : June 15, 1982

INVENTOR(S) : A. R. McFadden, et al.

It is certified that error appears in the above-identified patent and that said Letters Patent is hereby corrected as shown below:

Claim 52: "11-cyano-5-,6-dihydro..." should be
--11-cyano-5,6-dihydro...--

Claim 55: "...5-methyl-11[3-(1-..." should be
--...5-methyl-11-[3-(1-...--

Claim 71: "11-cyano-11[2-..." should be
--11-cyano-11-[2-...--

Claim 81: "...morpholinoethyl]-..." should be
--...morpholino)ethyl]-...--

Signed and Sealed this

Twenty-first Day of September 1982

[SEAL]

Attest:

Attesting Officer

GERALD J. MOSSINGHOFF

Commissioner of Patents and Trademarks